(12) United States Patent
Shuber

(10) Patent No.: US 7,811,757 B2
(45) Date of Patent: Oct. 12, 2010

(54) METHODS FOR DISEASE DETECTION

(75) Inventor: Anthony P. Shuber, Mendon, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 11/517,808

(22) Filed: Sep. 7, 2006

(65) Prior Publication Data

US 2007/0202513 A1     Aug. 30, 2007

Related U.S. Application Data

(63) Continuation of application No. 10/434,482, filed on May 7, 2003, now abandoned, which is a continuation of application No. 09/455,950, filed on Dec. 7, 1999, now Pat. No. 6,586,177.

(60) Provisional application No. 60/152,847, filed on Sep. 8, 1999.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search .............. 435/6, 435/91.2; 536/24.33, 23.1
See application file for complete search history.

(56) References Cited

U.S. PATENT DOCUMENTS

| | | |
|---|---|---|
| 3,413,464 A | 11/1968 | Hetensky |
| 4,101,279 A | 7/1978 | Aslam et al. |
| 4,309,782 A | 1/1982 | Paulin et al. |
| 4,333,734 A | 6/1982 | Fleisher |
| 4,358,535 A | 11/1982 | Falkow et al. |
| 4,445,235 A | 5/1984 | Slover et al. |
| 4,535,058 A | 8/1985 | Weinberg et al. |
| 4,578,358 A | 3/1986 | Oksman et al. |
| 4,683,195 A | 7/1987 | Mullis et al. |
| 4,683,202 A | 7/1987 | Mullis |
| 4,705,050 A | 11/1987 | Markham |
| 4,735,905 A | 4/1988 | Parker |
| 4,786,718 A | 11/1988 | Weinberg et al. |
| 4,857,300 A | 8/1989 | Maksem |
| 4,871,838 A | 10/1989 | Bos et al. |
| 4,935,342 A | 6/1990 | Seligson et al. |
| 4,981,783 A | 1/1991 | Augenlicht |
| 4,982,615 A | 1/1991 | Sultan et al. |
| 5,087,617 A | 2/1992 | Smith |
| 5,126,239 A | 6/1992 | Livak et al. |
| 5,137,806 A | 8/1992 | LeMaistre et al. |
| 5,149,506 A | 9/1992 | Skiba et al. |
| 5,196,167 A | 3/1993 | Guadagno et al. |
| 5,200,314 A | 4/1993 | Urdea |
| 5,213,961 A | 5/1993 | Bunn et al. |
| 5,248,671 A | 9/1993 | Smith |
| 5,272,057 A | 12/1993 | Smulson et al. |
| 5,302,509 A | 4/1994 | Cheeseman |
| 5,330,892 A | 7/1994 | Vogelstein et al. |
| 5,331,973 A | 7/1994 | Fiedler et al. |
| 5,348,855 A | 9/1994 | Dattagupta et al. |
| 5,352,775 A | 10/1994 | Albertsen et al. |
| 5,362,623 A | 11/1994 | Vogelstein et al. |
| 5,369,004 A | 11/1994 | Polymeropoulos et al. |
| 5,378,602 A | 1/1995 | Polymeropoulos et al. |
| 5,380,645 A | 1/1995 | Vogelstein |
| 5,380,647 A | 1/1995 | Bahar et al. |
| 5,382,510 A | 1/1995 | Levine et al. |
| 5,409,586 A | 4/1995 | Kamahori et al. |
| 5,416,025 A | 5/1995 | Krepinsky et al. |
| 5,458,761 A | 10/1995 | Kamahori et al. |
| 5,463,782 A | 11/1995 | Carlson et al. |
| 5,466,576 A | 11/1995 | Schulz et al. |
| 5,468,610 A | 11/1995 | Polymeropoulos et al. |
| 5,468,613 A | 11/1995 | Erlich et al. |
| 5,482,834 A | 1/1996 | Gillespie |
| 5,489,508 A | 2/1996 | West et al. |
| 5,492,808 A | 2/1996 | de la Chapelle et al. |
| 5,496,470 A | 3/1996 | Lenhart |
| 5,506,105 A | 4/1996 | Haydock |
| 5,508,164 A | 4/1996 | Kausch et al. |
| 5,512,441 A | 4/1996 | Ronai |
| 5,514,547 A | 5/1996 | Balazs et al. |
| 5,518,901 A | 5/1996 | Murtagh |
| 5,527,676 A | 6/1996 | Vogelstein et al. |
| 5,532,108 A | 7/1996 | Vogelstein |
| 5,538,851 A | 7/1996 | Fach et al. |

(Continued)

FOREIGN PATENT DOCUMENTS

AU     A-11325/95     4/1996

(Continued)

OTHER PUBLICATIONS

Aaltonen et al. (1994) "Replication Errors in Benign and Malignant Tumors from Hereditary Nonpolypopsis Colorectal Cancer Patients" Cancer Research 54: 1645-1648.

(Continued)

*Primary Examiner*—Suryaprabha Chunduru
(74) *Attorney, Agent, or Firm*—Choate Hall & Stewart LLP; Fangli Chen

(57) ABSTRACT

The present invention provides methods for detecting disease by analysis of a patient sample to determine the integrity of nucleic acids in the sample.

12 Claims, 13 Drawing Sheets

U.S. PATENT DOCUMENTS

| | | | |
|---|---|---|---|
| 5,559,014 A | 9/1996 | Estes et al. | |
| 5,580,729 A | 12/1996 | Vogelstein | |
| 5,589,335 A | 12/1996 | Kearney et al. | |
| 5,599,662 A | 2/1997 | Respess | |
| 5,612,473 A | 3/1997 | Wu et al. | |
| 5,635,352 A | 6/1997 | Urdea et al. | |
| 5,641,628 A | 6/1997 | Bianchi | |
| 5,645,995 A | 7/1997 | Kieback | |
| 5,670,325 A * | 9/1997 | Lapidus et al. | 435/6 |
| 5,688,643 A | 11/1997 | Oka et al. | |
| 5,709,998 A | 1/1998 | Kinzler et al. | |
| 5,710,028 A | 1/1998 | Eyal et al. | |
| 5,736,333 A | 4/1998 | Livak et al. | |
| 5,741,650 A | 4/1998 | Lapidus et al. | |
| 5,759,777 A | 6/1998 | Kearney et al. | |
| 5,800,347 A | 9/1998 | Skates et al. | |
| 5,804,383 A | 9/1998 | Gruenert et al. | |
| 5,830,665 A | 11/1998 | Shuber et al. | |
| 5,846,710 A | 12/1998 | Bajaj | |
| 5,856,104 A | 1/1999 | Chee et al. | |
| 5,858,663 A | 1/1999 | Nisson et al. | |
| 5,882,865 A | 3/1999 | Vogelstein et al. | |
| 5,888,778 A | 3/1999 | Shuber | |
| 5,910,407 A | 6/1999 | Vogelstein et al. | |
| 5,916,744 A | 6/1999 | Taylor et al. | |
| 5,925,517 A | 7/1999 | Tyagi et al. | |
| 5,928,870 A | 7/1999 | Lapidus et al. | |
| 5,942,396 A | 8/1999 | Shiff et al. | |
| 5,952,178 A | 9/1999 | Lapidus et al. | |
| 5,976,800 A | 11/1999 | Lau et al. | |
| 6,020,137 A | 2/2000 | Lapidus et al. | |
| 6,037,130 A | 3/2000 | Tyagi et al. | |
| 6,037,465 A | 3/2000 | Hillebrand et al. | |
| 6,084,091 A | 7/2000 | Muller et al. | |
| 6,100,029 A | 8/2000 | Lapidus et al. | |
| 6,143,496 A | 11/2000 | Brown et al. | |
| 6,143,529 A * | 11/2000 | Lapidus et al. | 435/91.2 |
| 6,146,828 A | 11/2000 | Lapidus et al. | |
| 6,150,100 A | 11/2000 | Ruschoff et al. | |
| 6,156,504 A | 12/2000 | Gocke et al. | |
| 6,177,251 B1 | 1/2001 | Vogelstein et al. | |
| 6,203,993 B1 | 3/2001 | Shuber et al. | |
| 6,214,187 B1 | 4/2001 | Hammond et al. | |
| 6,214,558 B1 | 4/2001 | Shuber et al. | |
| 6,228,596 B1 | 5/2001 | Macina et al. | |
| 6,235,474 B1 | 5/2001 | Feinberg | |
| 6,238,927 B1 | 5/2001 | Abrams et al. | |
| 6,251,660 B1 | 6/2001 | Muir et al. | |
| 6,268,136 B1 | 7/2001 | Shuber et al. | |
| 6,280,947 B1 | 8/2001 | Shuber et al. | |
| 6,291,163 B1 | 9/2001 | Sidransky | |
| 6,300,077 B1 | 10/2001 | Shuber et al. | |
| 6,303,304 B1 | 10/2001 | Shuber et al. | |
| 6,351,857 B2 | 3/2002 | Slaon, III et al. | |
| 6,406,857 B1 | 6/2002 | Shuber et al. | |
| 6,415,455 B1 | 7/2002 | Slaon, III et al. | |
| 6,428,964 B1 | 8/2002 | Shuber | |
| 6,448,002 B1 | 9/2002 | Hillebrand et al. | |
| 6,475,738 B2 | 11/2002 | Shuber et al. | |
| 6,482,595 B2 | 11/2002 | Shuber et al. | |
| 6,498,012 B2 | 12/2002 | Laken | |
| 6,503,718 B2 | 1/2003 | Shuber et al. | |
| 6,551,777 B1 | 4/2003 | Shuber et al. | |
| 6,586,177 B1 * | 7/2003 | Shuber | 435/6 |
| 6,440,706 B1 | 6/2004 | Vogelstein et al. | |
| 6,849,403 B1 | 2/2005 | Shuber | |
| 6,919,174 B1 * | 7/2005 | Shuber | 435/6 |
| 6,964,846 B1 | 11/2005 | Shuber | |
| 7,368,233 B2 | 5/2008 | Shuber et al. | |
| 2001/0018180 A1 | 8/2001 | Shuber et al. | |
| 2001/0039012 A1 | 11/2001 | Lapidus | |
| 2001/0042264 A1 | 11/2001 | Sloan et al. | |
| 2002/0001800 A1 | 1/2002 | Lapidus | |
| 2002/0004201 A1 | 1/2002 | Lapidus et al. | |
| 2002/0025525 A1 | 2/2002 | Shuber | |
| 2002/0040498 A1 | 4/2002 | Sloan et al. | |
| 2002/0045183 A1 | 4/2002 | Shuber et al. | |
| 2002/0048752 A1 | 4/2002 | Lapidus et al. | |
| 2002/0064787 A1 | 5/2002 | Shuber et al. | |
| 2002/0110810 A1 | 8/2002 | Shuber | |
| 2002/0119469 A1 | 8/2002 | Shuber et al. | |
| 2002/0119472 A1 | 8/2002 | Lapidus et al. | |
| 2002/0123052 A1 | 9/2002 | Laken | |
| 2002/0132251 A1 | 9/2002 | Shuber | |
| 2002/0164631 A1 | 11/2002 | Shuber et al. | |
| 2003/0044780 A1 | 3/2003 | Lapidus et al. | |
| 2003/0049659 A1 | 3/2003 | Lapidus et al. | |
| 2003/0087258 A1 | 5/2003 | Shuber | |
| 2004/0043467 A1 | 3/2004 | Shuber et al. | |
| 2005/0260638 A1 | 11/2005 | Shuber | |
| 2006/0121495 A1 | 6/2006 | Shuber | |
| 2007/0202513 A1 | 8/2007 | Shuber | |
| 2008/0241830 A1 | 10/2008 | Vogelstein et al. | |

FOREIGN PATENT DOCUMENTS

| | | |
|---|---|---|
| AU | 711754 | 7/1997 |
| AU | 704696 | 8/1997 |
| AU | 745862 | 9/1998 |
| AU | 744746 | 1/1999 |
| AU | 19942333 | 9/1999 |
| AU | 720489 | 6/2000 |
| CA | 2228769 | 2/1997 |
| CA | 2211702 | 7/1997 |
| DE | 19530132 C2 | 2/1997 |
| DE | 19712332 A | 10/1998 |
| DE | 19736691 A | 2/1999 |
| EP | 0259031 B1 | 3/1988 |
| EP | 0270017 | 6/1988 |
| EP | 0270017 A2 | 6/1988 |
| EP | 0270017 A3 | 6/1988 |
| EP | 0 284 362 A2 | 9/1988 |
| EP | 0 284 362 A3 | 9/1988 |
| EP | 0284362 A3 | 9/1988 |
| EP | 0337498 | 10/1989 |
| EP | 0390323 A2 | 10/1990 |
| EP | 0390323 A3 | 10/1990 |
| EP | 0391565 A2 | 10/1990 |
| EP | 0407789 A1 | 1/1991 |
| EP | 0407789 B1 | 1/1991 |
| EP | 0608004 A2 | 7/1994 |
| EP | 0643140 A | 3/1995 |
| EP | 0648845 A2 | 4/1995 |
| EP | 0664339 A1 | 7/1995 |
| GB | 2327497 | 1/1999 |
| JP | 3325270 | 9/2002 |
| WO | WO-90/09455 | 8/1990 |
| WO | WO-92/13103 | 8/1992 |
| WO | WO-92/16657 | 10/1992 |
| WO | WO-93/18186 | 9/1993 |
| WO | WO-93/20233 | 10/1993 |
| WO | WO-93/20235 | 10/1993 |
| WO | WO-94/00603 | 1/1994 |
| WO | WO-94/01447 | 1/1994 |
| WO | WO-94/09161 | 4/1994 |
| WO | WO-94/10575 | 5/1994 |
| WO | WO-94/11383 | 5/1994 |
| WO | WO-95/00669 A | 1/1995 |
| WO | WO-95/07361 | 3/1995 |
| WO | WO-95/09928 | 4/1995 |
| WO | WO-95/09929 | 4/1995 |
| WO | WO-95/12606 | 5/1995 |
| WO | WO-95/13397 | 5/1995 |
| WO | WO-95/13399 | 5/1995 |

| | | |
|---|---|---|
| WO | WO-95/15400 | 6/1995 |
| WO | WO-95/16792 | 6/1995 |
| WO | WO-95/18818 | 7/1995 |
| WO | WO-95/19448 | 7/1995 |
| WO | WO-95/25813 | 9/1995 |
| WO | WO-95/31728 | 11/1995 |
| WO | WO-96/01907 | 1/1996 |
| WO | WO-96/06951 | 3/1996 |
| WO | WO-96/08514 | 3/1996 |
| WO | WO-96/12821 | 5/1996 |
| WO | WO-96/13611 | 5/1996 |
| WO | WO-96/23895 A | 8/1996 |
| WO | WO-96/29430 A | 9/1996 |
| WO | WO-96/30545 | 10/1996 |
| WO | WO-97/07239 | 2/1997 |
| WO | WO-97/09449 | 3/1997 |
| WO | WO-97/09600 | 3/1997 |
| WO | WO-97/19191 A | 5/1997 |
| WO | WO-97/23651 | 7/1997 |
| WO | WO-97/25442 | 7/1997 |
| WO | WO-97/28280 | 8/1997 |
| WO | WO-97/28450 | 8/1997 |
| WO | WO-97/34015 A1 | 9/1997 |
| WO | WO-98/08971 | 3/1998 |
| WO | WO-98/38338 | 9/1998 |
| WO | WO-98/39478 | 9/1998 |
| WO | WO-98/58081 | 12/1998 |
| WO | WO-98/58084 | 12/1998 |
| WO | WO-99/07894 | 2/1999 |
| WO | WO-99/07895 | 2/1999 |
| WO | WO-99/10528 | 3/1999 |
| WO | WO 99/13113 | 3/1999 |
| WO | WO-99/16906 | 4/1999 |
| WO | WO-99/20798 | 4/1999 |
| WO | WO-99/26724 | 6/1999 |
| WO | WO-99/28507 | 6/1999 |
| WO | WO-99/29903 | 6/1999 |
| WO | WO-99/45374 | 9/1999 |
| WO | WO-99/53316 | 10/1999 |
| WO | WO-99/55912 | 11/1999 |
| WO | WO-99/66077 | 12/1999 |
| WO | WO-99/66078 | 12/1999 |
| WO | WO-99/66079 | 12/1999 |
| WO | WO-00/09751 | 2/2000 |
| WO | WO-00/11215 | 3/2000 |
| WO | WO-00/31298 | 6/2000 |
| WO | WO-00/31303 | 6/2000 |
| WO | WO-00/31305 | 6/2000 |
| WO | WO-00/32820 | 6/2000 |
| WO | WO-00/50640 | 8/2000 |
| WO | WO-00/50870 | 8/2000 |
| WO | WO-00/58514 | 10/2000 |
| WO | WO-00/60118 | 10/2000 |
| WO | WO-00/61808 | 10/2000 |
| WO | WO-00/66005 | 11/2000 |
| WO | WO-00/70096 | 11/2000 |
| WO | WO-00/70096 A3 | 11/2000 |
| WO | WO-01/11083 A2 | 2/2001 |
| WO | WO-01/11083 A3 | 2/2001 |
| WO | WO-01/18252 | 3/2001 |
| WO | WO-01/42502 | 6/2001 |
| WO | WO-01/42502 A3 | 6/2001 |
| WO | WO-01/42503 | 6/2001 |
| WO | WO-01/42503 A3 | 6/2001 |
| WO | WO-01/42781 | 6/2001 |
| WO | WO-01/64950 | 9/2001 |
| WO | WO-01/64950 A2 | 9/2001 |
| WO | WO-02/55740 | 7/2002 |
| WO | WO-02/59379 | 8/2002 |
| WO | WO-02/74995 | 9/2002 |
| WO | WO-02/92858 | 11/2002 |

OTHER PUBLICATIONS

Aaltonen et al. (1998) "Incidence of Hereditary Nonpolyposis Colorectal Cancer and the Feasibility of Molecular Screening for the Disease" The New England Journal of Medicine 338: 1481-1487.

Allen et al. (1997) "Morphological and biochemical characterization and analysis of apoptotis." J Pharm. & Toxicol. Methods, vol. 37, No. 4, pp. 215-228.

Ambrosini et al. "A navel anti-apoptosis gene, surviving, expressed in cancer and lymphoma" Nature Medicine, vol. 3, No. 8, pp. 917-921, Aug. 1997.

Anker et al. (1999) "Detection of Circulating Tumour DNA in the Blood (plasma/serum) of Cancer Patients," Cancer and Metastasis Reviews, vol. 18, pp. 65-73.

Arber et al. "A K-ras Oncogene Increases Resistance to Sulindac-Induced Apoptosis in Rat Enterocytes," Gastroenterology, vol. 113, No. 6, pp. 1892-1900, Dec. 1997.

Ausubel et al., (1995), Short Protocols in Molecular Biology, 3d ed., pp. 2-3 -2-12, 3-30 -3-33.

Azhikina et al. (1996), "Factors Affecting the Priming Efficiency of Short Contiguous Oligonucleotide Strings in the Primer Walking Strategy of DNA Sequencing," DNA Sequence 6:211-216.

Barry et al. "Identification of Deoxyribonuclease 11 as an Endonucleas Involved in Apoptosis," Archives of Biochemistry and Biophysics, vol. 300, No. I, pp. 440-450, Jan. 1993.

Bernstein et al. "A Bile Acid-induced Apoptosis Assay for Colon-Cancer Risk and Associated Quality Control Studies," Cancer Research, vol. 59, pp. 2353-2357, May 15, 1999.

Bertario et al. (1999) "Risk of Colorectal Cancer Following Colonoscopic Polypectomy" Tumori 85: 157-162.

Beskin et al., (1995), "On the Mechanism of the Modular Primer Effect," Nucleic Acids Research, vol. 23 No. 15, 2881-2885.

Blum (1995) "Colorectal Cancer: Future Population Screening for Early Colorectal Cancer" European Journal of Cancer, vol. 31A, pp. 1369-1372.

Boom et al., (Mar. 1990) "Rapid and Simple Method for Purification of Nucleic Acids" J Clin. Microbiol, vol. 28, No. 3, pp. 495-503.

Bos et al., (May 28, 1987) "Prevalence of ras Gene Mutations in Human Colorectal Cancers," Nature, vol. 327, pp. 293-297.

Caldas et al., (Jul. 1, 1994) "Detection of K-ras Mutations in the Stool of Patients with Pancreatic Adenocarcinoma and Pancreatic Ductal Hyperplasia" Cancer Research, vol. 54, pp. 3568-3573.

Capozzi et al. (1999) "Evaluation of the Replication Error Phenotype in Relation to Molecular and Clinicopathological Features in Hereditary and Early Onset Colorectal Cancer" European Journal of Cancer 35: 289-295.

Cave et al., (1994) "Reliability of PCR Directly from Stool Samples: Usefulness of an Internal Standard," BioTechniques, vol. 16, No. 5, pp. 809-810.

Cawkwell et al. (1994) "Frequency of allele loss of DCC, p53, RBI, WTI, NF1, NM23 and APC/MCC in colorectal cancer assayed by fluorescent multiplex polymerase chain reaction." Brit. J. Can., vol. 70, No. 5, pp. 813-818.

Chapelle (1999) "Testing Tumors for Microsatellite Instability" European Journal of Human Genetics 7: 407-408.

Charlesworth et al., (Sep. 15, 1994) "The Evolutionary Dynamics of Repetitive DNA in Eukaryotes," Nature, vol. 371, pp. 215-220.

Chen et al. (1997) "Microsatellite Instability in Sporadic-Colon-Cancer Patients With and Without Liver Metastases" International Journal of Cancer 74: 470-474.

Chen et al., (Jul. 15, 1996), "Detection of Single-Base Mutations by a Competitive Mobility Shift Assay," Analytical Biochemistry, CIS, Academic, Press, vol. 239, No. 1, pp. 61-69.

Coll et al., (Oct. 1989) "Evaluation of a Rapid Method of Extracting DNA from Stool Samples for Use in Hybridization Assays," Journal of Clinical Microbiology, vol. 27, No. 10, pp. 2245-2248.

Coombs et al. (May 21, 1996) "A Rapid, Simple, and User-Friendly Method for DNA Extraction from Clinical Stool Samples," ASM 1996 General Meeting, New Orleans, LA.

Coughlin et al. (1999) "Public Health Perspectives on Testing for Colorectal Cancer Susceptibility Genes" American Journal of Preventive Medicine 16: 99-104.

Croitoru et al. "Reduce, Reuse, and Recycle: Shedding Light on Shedding Cells," Gastroenterology, vol. 105, pp. 1243-1246, Oct. 1993.

Cunningham C. and M.G. Dunlop, (1996) "Molecular Genetic Basis of Colorectal Cancer Susceptibility," British Journal of Surgery, vol. 83, pp. 321-329.

Deng et al. (Dec. 20, 1996) "Loss of Heterozygosity in Normal Tissue Adjacent to Breast Carcinomas," Science, vol. 274, pp. 2057-2059.

Dennin (1979) "DNA of Free and Complexed Origin in Human Plasma: Concentration and Length Distribution," Klin. Wochenschr. vol. 57, pp. 451-456.

Depraetere "Eat me- Signals of apoptotic bodies," Nature Cell Biology, vol. 2, p. E 104, Jun. 2000.

Deuter et al., (1995) "A Method for Preparation of Fecal DNA Suitable for PCR," Nucleic Acids Research, vol. 23, No. 18, pp. 3800-3801.

Dib et al., (Mar. 14, 1996) "A Comprehensive Genetic Map of the Human Genome Based on 5,264 Microsatellites," Nature vol. 380, pp. 152-154.

Ditkoff et al. (1996) Surgery vol. 1207 No. 6, pp. 959-965.

Duffy (1995) "Can Molecular Markers Now be Used for Early Diagnosis of Malignancy?" Clin. Chem,. vol. 41, No. 10, pp. 1410-1413.

Eads et al. (1999) "CpG island hypermethylation in human colorectal tumors is not associated with DNA methyltransferase overexpression." Cancer Research, vol. 59, No. 10, pp. 2301-2306.

Echeverria et al. (Sep. 1985) "DNA Hybridization in the Diagnosis of Bacterial Diarrhea," Clinics in Laboratory Medicine, vol. 5, No. 3, Sep. 1985, pp. 447-462.

Eguchi et al., (Apr. 15, 1996) "Mutations of the p53 Gene in the Stool of Patients with Resectable Colorectal Cancer," Cancer Supplement, vol. 77, No. 8, pp. 1707-1710.

Emlen et al. (1984) "Effect of DNA Size and Strandedness on the in vivo Clearance and Organ Localization of DNA," Clin. Exp. Immunol., vol. 56, pp. 185-192.

Enari et al., (Jan. 1, 1998) "A Caspase-Activated DNase that Degrades DNA During Apoptosis, and its inhibitor ICAD," Nature, vol. 391, pp. 43-50.

Fearon (1995) "16 Molecular Abnormalities in Colon and Rectal Cancer," The Molecular Basis of Cancer, pp. 340-357.

Finkel "Does Cancer Therapy Trigger Cell Suicide?," Science, vol. 286, pp.2256-2258, Dec. 17, 1999.

Fournie et al. (1995) "Plasma DNA as a Marker of Cancerous Cell Death. Investigations in Patients Suffering from Lung Cancer and in Nude Mice Bearing Human Tumours," Cancer Letters, vol. 91, pp. 221-227.

Garewal et al. "Reduced Bile Acid-induced Apoptosis in "Normal" Colorectal Mucosa: A Potential Biological Marker for Cancer Risk" Cancer Research, vol. 56, pp. 1480-1483, Apr. 1, 1996.

Giacona et al. (1998) "Cell-Free DNA in Human Blood Plasma: Length Measurements in Patients with Pancreatic Cancer and Healthy Controls," Pancreas, vol. 17, No. 1, pp. 89-97.

Grossman et al. (1988), "Colonoscopic Screening of persons With Suspected Risk Factors for Colon Cancer" Gastroenterology 94: 395-400.

Gyllensten et al. (1995) "Sequencing of in Vitro Amplified DNA," Recombinant DNA Methodology II, (Wu, ed.), pp. 565-578.

Halim "Apoptosis: Orderly Dismantling" The Scientist, p. 19, Feb. 7, 2000.

Hall et al. "Regulation of cell number in the mammalian gastrointestinal tract: the importance of apoptosis," Journal of Cell Science, vol. 107, pp. 3569-3577, 1994.

Hasegawa et al., (1995) "Detection of K-ras Mutations in DNAs Isolated From Feces of Patients with Colorectal Tumors by Mutant-Allele-Specific Amplification (MASA)," Oncogene, vol. 10, pp. 1441-1445.

Hetts "To Die or Not to Die, An Overview of Apoptosis and Its Role in Disease," JAMA, vol. 279, No. 4, pp. 300-307, Jan. 28, 1998.

Hibi et al. (Apr. 1998) "Molecular Detection of Genetic Alterations in the Serum of Colorectal Cancer Patients," Cancer Research, vol. 58, pp. 1405-1407.

Hitchcock "Actin- Deoxyribonuclease I Interaction," The Journal of Biochemical Chemistry, vol. 255, No. 12, pp. 5668-5673, 1980.

Hoang et al. (1997) "BAT-26, an Indicator of the Replication Error Phenotype in Colorectal Cancers and Cell Lines" Cancer Research 57: 300-303.

Honchel et al. (1995) "Genomic Instability in Neoplasia," Seminars in Cell Biology, vol. 6, pp. 45-52.

Hoss et al. (Sep. 17, 1992) "Excrement Analysis by PCR" Scientific Correspondence pp. 199.

Hunsaker et al. (1989) "Use of Reversible Target Capture to Detect Subattomole Quantities of Target Nonradioleotopically in Crude Specimens in One Hour," Abstracts of the 89'h Meeting of the American Society for Microbiology, D-169, p. 110.

Iino et al. (1999) "DNA Microsatellite Instability in Hyperplastic Polyps, Serrated Adenomas, and Mixed Polyps: a Mild Mutator Pathway for Colorectal Cancer?" Journal of Clinical Pathology 52: 5-9.

Iniesta et al. (1998) "Genetic Abnormalities and Microsatellite Instability in Colorectal Cancer" Cancer Detection and Prevention 22: 383-395.

Ishimaru et al. (1995) "Microsatellite Instability in Primary and Metastatic Colorectal Cancers" International Journal of Cancer 64: 153-157.

Ito et al. (1999) "Profile of Circulating Levels of Interleukin-1 Receptor Antagonists and Interleukin-6 in Colorectal Cancer Patients," Scand J. Gastroenterol., vol., 1, pp. 1139-1143.

Iwanaga et al. "A Novel Mechanism for Disposing of Effete Epithelial Cells in the Small Intestine of Guinea Pigs," Gastroenterology, vol. 105, No. 4, pp. 1089-1097, 1993.

Jarvinen et al. (1995) "Screening Reduces Colorectal Cancer Rate in Families With Hereditary Nonpolyposis Colorectal Cancer" Gastroenterology 108: 1405-1411.

Jernvall et al. (1999) "Microsatellite Instability: Impact on Cancer Progression in Proximal and Distal Colorectal Cancers" European Journal of Cancer 35: 197-201.

Jessup et al. (Sep./Oct. 1992) "The Biology of Colorectal Carcinoma," Current Problems in Cancer pp. 263-328.

Jonsson et al. (Jan. 1995) "From Mutation Mapping to Phenotype Cloning," Proc. Natl. Acad. Sci., vol. 92 pp. 83-85.

Kataoka et al. "Association of high molecular weight DNA fragmentation with apoptotic or non-apoptotic cell death induced by calcium ionophore" FEBS Letters, vol. 364, pp. 264-267, 1995.

Kawasaki et al. "Inhibition of Apoptosis by Surviving Predicts Shorter Survival Rates in Colorectal Cancer," Cancer Research, vol. 58, pp. 5071-5074, Nov. 15, 1998.

Kim et al. (1998) "Microsatellite Instability in Young Patients With Colorectal Cancer" Pathology International 48: 586-594.

Kishi et al. "Human Serum Deoxyribonuelease I (DNase I) Polymorphism: Pattern Similarities among Isozymes from Serum, Urine, Kidney, Liver, and Pancreas," Am. J. Hum. Genet., vol. 47, pp. 121-126,1990.

Komano et al. "Homeostatic regulation of intestinal epithelia by intraepithelial γδ T cells" Proc. Natl. Acad. Sci. USA 92, vol. 92, pp. 6147-6151, Jun. 1995.

Konishi et al. (1996) "Molecular Nature of Colon Tumors in Hereditary Nonpolyposis Colon Cancer, Familial Polyposis, and Sporadic Colon Cancer" Gastroenterology 1 11: 307-317.

Lamberti et al. (1999) "Microsatellite Instability—a Useful Diagnostic Tool to Select Patients at High Risk for Hereditary Non-Polyposis Colorectal Cancer: A Study in Different Groups of Patients With Colorectal Cancer" Gut 44: 839-843.

Lefrere et al. (Oct. 1998)"Screening Blood Donations for Viral Genomes: Multicenter Study of Real-Time Simulation Using Pooled Samples on the Model of HCV RNA Detection" Transfusion, vol. 38, pp. 915-923.

Lengauer et al., (Dec. 17, 1998) "Genetic Instabilities in Human Cancers," Nature, vol. 396, pp. 643-649.

Leon et al. (Mar. 1977) "Free DNA in the Serum of Cancer Patients and the Effect of Therapy," Cancer Research, vol. 37, pp. 646-650.

Leong et al., (1993) "Detection of MYCN Gene Amplification and Deletions of Chromosome Ip in Neuroblastoma by in Situ Hybridization Using Routine Histologic Sections," Laboratory Investigations, vol. 69, No. 1, pp. 43-50.

Li et al. (Aug. 1996) "Rapid Detection of Mycobacterium Avium in Stool Samples from AIDS Patients by Immunomagnetic PCR," J Clin. Microbiol., vol. 34, No. 8, pp. 1903-1907.

Lin et al. (1998) "Colorectal and Extracolonic Cancer Variations in MLH I/MSH2 Hereditary Nonpolyposis Colorectal Cancer Kindreds and the General Population" Diseases of the Colon & Rectum 41: 428-433.

Lipkin "Biomarkers of Increased Susceptibility to Gastrointestinal Cancer: New Application to Studies of Cancer Prevention in Human Subjects," Cancer Research, vol. 48, pp. 235-245, Jan. 15, 1998.

Litia et al. (1992) "Simultaneous Detection of Two Cystic Fibrosis Alleles Using Dual-Label Time-Resolved Fluorometry," Molecular and Cellular Probes, vol. 6, pp. 505-512.

Lleonart et al. (1998) "Microsatellite Instability and p53 Mutations in Sporadic Right and Left Colon Carcinoma" American Cancer Society 83: 889-895.

Loktionov et al. (1995) "Early Detection of Cancer-Associated Gene Alterations in DNA Isolated from Rat Feces During Intestinal Tumor Induction with 1,2-Dimethylhydrazine," International Journal of Oncology, vol. 6, pp. 437-445.

Loktionov et al. (Feb. 1998) "Quantitation of DNA from Exfoliated Colonocytes Isolated from Human Stool Surface as a Novel Noninvasive Screening Test for Colorectal Cancer," Clinical Cancer Research, vol. 4, pp. 337-341.

Maebo (1990) "Plasma DNA Level as a Tumor Marker in Primary Lung Cancer," Japanese; English abstract attached.

Mannherz et al. "A Specific 1:1 G-Actin: DNAase I Complex Formed by the Action of DNAase I on F-Actin," F'EBS Letters, vol. 60, No. 1, pp. 34-38, Dec. 1975.

Mannherz et al. "The Interaction of Bovine Pancreatic Deoxyribonuclease I and Skeletal Muscle Actin" Eur. J. Biochem, vol. 104, pp. 367-379, 1980.

Mao et al. (Feb. 2, 1996) "Molecular Detection of Primary Bladder Cancer by Microsatellite Analysis," Science, vol. 271, pp. 659-662.

Metspalu "Arrayed Primer Extension (APEX) for Mutation Detection Using Gene-Specific DNA Chips" European Journal of Human Genetics, vol. 6, No. Sup 1, 1998, p. PL36 XP000892253 Abstract.

Morandi et al. (Jun. 1998) "Detection of HIV Type I RNA in Pools of Sera Negative for Antibiotics to HIV-1 and HIV-2," J of Clinical Microbiology, vol. 36, No. 6, pp. 1534-1538.

Morrissey et al. (May 14-18, 1989) "Novel Hybridization Technique with Subattomole Sensitivity in Specimens" American Society for Microbiology, 891 Annual Meeting, Abstract D-168, p. 110.

Morrissey, et al. (Sep. 1989) "Nucleic Acid Hybridization Assays Employing dA-Tailed Capture Probes," Analytical Biochemistry, vol. 181, No. 2, pp. 345-359.

Mulcachy et al. (Feb. 1998) "A Prospective Study of K-ras Mutations in the Plasma of Pancreatic Cancer Patients," *Clinical Cancer Research* vol. 4, pp. 271-275.

Myers, R.M., (Feb. 12, 1993) "The Pluses of Subtraction," Science, vol. 259, pp. 942-943.

Naber (Dec. 1, 1994) "Molecular Pathology—Detection of Neoplasia," New England Journal of Medicine, vol. 331, No. 22, pp. 1508-1510.

Nollau et al. (1996) Detection of K-ras Mutations in Stools of Patients with Colorectal Cancer by Mutant-Enriched PCR, Int. J.Cancer, vol. 66, pp. 1524-1529.

Nollau et al. (May 1996) "Isolation of DNA from Stool and Bodily Fluids for PCR Amplication," BioTechniques, vol. 20, No. 5, pp. 784-788.

Olive (Feb. 1989) "Detection of Enterotoxigenic *Escherichia coli* after Polymerase Chain Reaction Amplification with a Thermostable DNA Polymerase," Journal of Clinical Microbiology, vol. 27, No. 2, pp. 261-265.

Orlow, et al. (Oct. 18, 1995) "Deletion of the p16 and p15 Genes in Human Bladder Tumors Journal of the National Cancer Institute, ," vol. 87, No. 20, pp. 1524-1529.

Orou, et al. (1995) "Allele-Specific Competitive Blocker PCR: A One-Step Method With Applicability to Pool Screening" Human Mutation vol. 6, 163-169.

Paabo et al. (1988) "Mitochondrial DNA Sequences from a 7000-year old Brain," Nucleic Acids Research, vol. 16, No. 20, pp. 9775-9777.

Pacek et al. (May 1993) "Determination of Allele Frequencies at Loci with Length Polymorphism by Quamitive Analysis of DNA Amplified from Pooled Samples," PCR Methods and Applications, vol, 2, No. 4, pp. 313-317.

Park et al. "Detergent and Enzyme Treatment of Apoptotic Cells for Observation of DNA Fragmentation" BioTechniques, vol. 24, No. 4, pp. 558-559,1998.

Park et al. (1999) "Gene-Environment Interaction in Hereditary Nonpolyposis Colorectal Cancer with Implications for Diagnosis and Genetic Testing" International Journal of Cancer 82: 516-519.

Payne et al. Role of Apoptosis in Biology and Pathology: Resistance to Apoptosis in Colon Carcinogenes & Ultrastructural Pathology, vol. 19, pp. 221-248, 1995.

Peitsch et al. "Characterization of the endogenous deoxyribonuclease involved in nuclear DNA degradation during apoptosis (programmed cell death)," The EMBO Journal, vol. 12, No. 1, pp. 371-377, 1993.

Peitsch et al. "Functional characterization of serum DNase 1 in MRI," Biochemical and Biophysical Research Communications, vol. 186, No. 2, pp. 739-745, Jul. 31, 1992.

Peitsch et al. "The apoptosis endonucleases: cleaning up after cell death?," Trends in Cell Biology, vol, 4, pp. 37-41, Feb. 4, 1994.

Peltomaki et al. (1997) "Mutations Predisposing to Hereditary Nonpolyposis Colorectal Cancer: Database and Results of a Collaborative Study" Gastroenterology 113: 1146-1158.

Pharmacia (1991/1992) Molecular and Cell Biology Catalogue, pp. 8.3-8.6.

Pharmacia (1998) BioDirectory, pp. 104-109.

Piao et al. (Sep. 1997) "Relationship between Loss of Heterozygosity of Tumor Suppressor Genes and Histologic Differentiation in Hepatocellular Carcinoma," Cancer, vol. 80, No. 5, pp. 865-872.

Polzar et al. "Distribution of deoxyribonuclease 1 in rat tissues and its correlation to cellular turnover and apoptosis (programmed cell death)," European Journal of Cell Biology, vol. 64, pp. 200-210, 1994.

Polzar et al. "Overexpression of deoxyribonuciease I (DNase I) transfected into COS-cells: its distribution during apoptotic cell death," European Journal of Cell Biology, vol. 62, pp. 397-405, 1993.

Ponz de Leon et al. (1998) "Frequency and Type of Colorectal Tumors in Asymptomatic High-Risk Individuals in Families with Hereditary Nonpolyposis Colorectal Cancer" Cancer Epidemiology, Biomarkers & Prevention 7: 639-641.

Ponz de Leon et al. (1999) "Hereditary Colorectal Cancer in the General Population: From Cancer Registration to Molecular Diagnosis" Gut 45: 32-38.

Pyatt et al. (1999) "Polymorphic Variation at the BAT-25 and Bat-26 Loci in Individuals of African Origin" American Journal of Pathology 155: 349-353.

Raff (Nov. 12, 1998) "Cell Suicide for Beginners," Nature, vol. 396, pp. 119-122.

Raptis et al. (Dec. 1980) "Quantitation and Characterization of Plasma DNA in Normals and Patients with Systemic Lupus Erythematosus," J. Clin. invest., vol. 66, pp. 1391-1399.

Rashid et al. (1999) "Genetic Epidemiology of Mutated K-ras Proto-Oncogene, Altered Suppressor Genes, and Microsatellite Instability in Colorectal Adenomas" Gut 44: 826-833.

Ravelingien et al. (1995) "Contribution of Molecular Oncology in the Detection of Colorectal Carcinomas," Acta Gastro-Enterologica Belgic a, vol. 58, pp. 270-273.

Rhyu (Mar. 6, 1996) "Molecular Mechanisms Underlying Hereditary Nonpolyposis Colorectal Carcinoma," Journal of the National Cancer Institute, vol. 88, No. 5, pp. 240-251.

Ridanpaa et al. (1995) "Detection of Loss of Heterozygosity in the p53 Tumor Suppressor Gene Using a PCR-based Assay," Path. Res. Pract., vol. 191, pp. 399-402.

Riegler et al. (1999) "Prevalence of HNPCC in a Series of Consecutive Patients on the First Endoscopic Diagnosis of Colorectal Cancer: A Multicenter Study" Endoscopy 31: 337-341.

Rinaldy et al. (1988), "Gene Cloning Using cDNA Libraries in a Differential Competition Hybridization Strategy: Application to Cloning XP-A Related Genes," DNA 7(8):563-70.

Rodriguez-Bigas et al. (1997) "A National Cancer Institute Worship on Hereditary Nonpolyposis Colorectal Cancer Syndrome: Meeting Highlights and Bethesda Guidelines" Journal of the National Cancer Institute 89:1758-1762.

Ruzicka et al. (1992) "Apolipoprotein Allele Specific PCR: Large-Scale Screening of Pooled Blood Samples," J. of Lipid Research, vol. 33, pp. 1563-1567.

Saitoh et al. "Analysis of Bcl-2, Bax and Survivin genes in uterine cancer" International Journal of Oncology, vol. 15, pp. 137-141, 1999.

Salahshor et al. (1999) "Microsatellite Instability in Sporadic Colorectal Cancer is Not an Independent Prognostic Factor" British Journal of Cancer 81: 190-193.

Sales et al. (Jul. 1999) "Blood Dissemination of Colonic Epithelial Cells During No-touch surgery for Rectosigmoid Cancer," The Lancet, vol. 354, p. 392.

Samiotaki et al. (1994) "Dual-Color Detection of DNA Sequence Variants by Ligase-Mediated Analysis," Genomics 20:238-42.

Samowitz et al. (1995) "Microsatellite Instability in Human Colonic Cancer Is Not a Useful Clinical Indicator of Familial Colorectal Cancer" Gastroenterology 109: 1765-1771.

Samowitz et al. (1997) "Microsatellite Instability in Colorectal Adenomas" Gastroenterology 112:1515-1519.

Samowitz et al. (1999) "BAT-26 and BAT-40 Instability in Colorectal Adenomas and Carcinomas and Germline Polymorphisms" American Journal of Pathology 154: 1637-1641.

Sanger et al. (Dec. 1977) "DNA Sequencing with Chain-Terminating Inhibitors" Proc. Natl. Acad. Sci. USA, vol. 74, No. 12, pp. 5463-5467.

Santagati et al. (1997) "Quantitation of Low Abundance mRNAs in Glial Cells Using Different Polymerase chain Reaction (PCR)-Based Methods," Elsevier Science—Brain Research Protocols, 217-223.

Schmitt et al. (1998) "Bax-alpha promotes apoptosis induced by cancer chemotherapy and accelerates the activation of caspase 3-like cysteine proteases in p53 double mutant B lymphoma Namalwa cells." Cell Death & Diff., vol. 5, No. 6, pp. 506-516.

Segel (1976), "Double Label Analysis," Biochemical Calculations, 2d ed., pp. 373-376.

Sen "Programmed Cell Death: Concept, Mechanism and Control" Biol. Rev., vol. 67, pp. 287-319, 1992.

Shapiro et al. (Jun. 1983) "Determination of Circulating DNA Levels in Patients with Benign or Malignant Gastrointestinal Disease" Cancer, vol. 51, No. 11, pp. 2116-2120.

Shaw et al. (1998) "Allele Frequency Distribution in Pooled DNA Samples, Applications to Mapping Complex Disease Genes." Genome Research. vol. 8. pp. 111-123m.

Sidransky (1997) "Nucleic acid-based methods for the detection of cancer." Science, vol. 278, No. 5340, pp. 1054-1057.

Sidransky et al. (Apr. 3, 1992) "Identification of ras Oncogene Mutations in the Stool of Patients with Curable Colorectal Tumors," Science, vol. 256, pp. 102-105.

Skoletsky et al. (1998) "High frequency of detecting amplifiable DNA in stools of apparently normal individuals." Gastroenterology, vol. 114, No. 4, p. A681.

Smith-Ravin et al. (1995) "Detection of c-Ki-ras Mutations in Fecal Samples from Sporadic Colorectal Cancer Patients," Gut, vol. 36, pp. 81-86.

Strater et al. "Rapid Onset of Apoptosis in Vitro Follows Disruption of B1 Integrin/Matrix Interactions in Human Colonic Crypt Cell" Gastroenterology, vol. 110, No. 6, pp. 1776-1784, Jun. 1996.

Stroun et al. (1987) "Isolation and Characterization of DNA from the Plasma of Cancer Patients," Eur. J. Cacner Clin. Oncol., vol. 23, No. 6, pp. 707-712.

Syngal et al. (1998) "Benefits of Colonoscopic Surveillance and Prophylactic Colectomy in Patients With Hereditary Nonpolyposis Colorectal Cancer Mutations" Annals of Internal Medicine 129: 787-796.

Syngal et al. (1999) "Interpretation of Genetic Test Results for Hereditary Nonpolyposis Colorectal Cancer" JAMA 282: 247.

Takeda et al. (1993) "Detection of K-ras Mutation in Sputum by Mutant-Allele-Specific Amplification (MASA)," Human Mutation, vol. 2, pp. 112-117.

Thibodeau et al., (May 7, 1993) "Microsatellite Instability in Cancer of the Proximal Colon," Science, vol. 260, pp. 816-819.

Tompkins et al. (1986) "Approaches to the Detection of Enteric Pathogens, Including Campytobacter, using Nucleic Acid Hybridization," Diagn. Microbiol, Infect. Dis., vol. 4, pp. 715-785.

Tsujitani et al. "Apoptotic Cell Death and Its Relationship to Carcinogenesis in Colorectal Carcinoma," Cancer Supplement, vol. 77, No. 8, pp. 1711-1716, Apr. 15, 1996.

Vasen et al. (1993) "Surveillance in Hereditary Nonpolyposis Colorectal Cancer: An International Cooperative Study of 165 Families" Diseases of the Colon & Rectum) 36: 1-4.

Vasen et al. (1998) "A Cost-Effectiveness Analysis of Colorectal Screening of Hereditary Nonpolyposis Colorectal Carcinoma Gene Carriers" American Cancer Society 82: 1632-1637.

Vasen et al. (1999) "New Clinical Criteria for Hereditary Nonpolyposis Colorectal Cancer (HNPCC, Lynch Syndrome) Proposed by the International Collaborative Group on HNPCC" Gastroenterology 116: 1453-1456.

Vera-Garcia, et al. (May 16-20 1993) "Development and Evaluation of an Instrument Designed to Reproducibly Release Nucleic Acids from Microorganisms" American Society for Microbiology Polymerase Chain Reaction, 93rd General Meeting, Session 214, Abstract C-217, p. 484.

Vet et al. (1998) "Comparative analysis of p53 mutations in bladder washings and histologic specimens" Am. J. Clin. Poth. vol. 110, No. 5, pp. 647-651.

Villa et al. (May 1996) "Identification of Subjects at Risk for Colorectal Carcinoma Through a Test Based on K-ras Determination in the Stool," Gastroenterology, vol. 110, No. 5, pp. 1346-1353.

Vogelstein et al. (1979) "Preparative and Analytical Purification of DNA from Agarose," Proc. Natl. Acad. Sci. USA, vol. 76, No. 2, pp. 615-619.

Vogelstein, et al. (Aug. 1999) "Digital PCR," Proc. Natl. Acad. Sci. USA, vol. 96, pp. 9236-9241.

Wagner et al. "Regulation of Gastric Epithelial Cell Growth by Helicobacter pylori: Evidence for a Major Role of Apoptosis," Gastroenterology, vol. 113, No. 6, pp. 1836-1847, Dec. 1997.

Wallace et al. (1979) "Hybridization of Synthetic Oligodeoxyribonucleotides to OX 174 DNA: the Effect of Single Base Pair Mismatch," Nucleic Acids Research, vol. 6, No. 11, pp. 3543-3557.

Walsh et al. (1991) "Chelex® 100 as a Medium for Simple Extraction of DNA for PCR-Based Typing from Forensic Material," BioTechniques, vol. 10, No. 4, pp. 506-513.

Walsh et al. (Feb. 6, 1992) "Preferential PCR Amplification of Alleles: Mechanisms and Solutions," PCR Methods and Applications, pp. 241-250.

Walton et al. (1997) "A PCR-Based Method for Detecting Rare Genotypes in Large Samples of Individuals," Mol. Ecology, vol. 6, No. 2, pp. 195-197.

Wang et al. (May 15, 1998) "Large-Scale Identification, Mapping, and Genotyping of Single-Nucleotide Olymorphisms in the Human Genome," Science, vol. 280, pp. 1077-1082.

Watson et al. "Isolation of Differentiality Expressed Sequence Tags from Human Breast Cancer," Advances in Brief XP 000576043 pp. 4598-4602.

Wijnen et al. (1999) "Familial Endometrial Cancer in Female Carriers of MSH6 Germline Mutations" Nature Genetics 23: 142-144.

Young et al. (1992) "The Genetics, Epidemiology, and Early Detection of Gastrointestinal Cancers" Current Opinion in Oncology, vol. 4, pp. 728-735.

Zhang et al. "Quantitative determination of apoptotic death in cultured human pancreatic cancer cells by propidium iodide and digitonin," Cancer Letters, vol. 142, pp. 129-137, 1999.

Zhou et al. (1997) "Allelic Profiles of Mononucleotide Repeat Microsatellites in Control Individuals and in Colorectal Tumors With and Without Replication Errors" Oncogene 15: 1713-1718.

Zhou et al. (1998) "Determination of the Replication Error Phenotype in Human Tumors Without the Requirement for Matching Normal DNA by Analysis of Mononucleotide Repeat Microsatellites" Genes. Chromosomes & Cancer 21: 101-107.

Alquist et al., "Colorectal Cancer Screening by Detection of Altered Human DNA in Stool: Feasibility Multitarget Assay Panel," Presented at Digestive Disesase Week Annual Conference, Orlando, FL, May 19, 1999 (Gastroenterology, 119, pp. 1219-1227 (2000).

Alquist et al., "Universal Detection of Aerodigestive Cancers by Assay of Nanopoptotic Human DNA in Stool," Presented at Digestive Disesase Week Annual Conference, San Diego, CA, May 2000.

Makristhathis et al., "Detection of Helicobacter pylori in Stool Specimens by PCR and Antigen Enzyme Immunoassay," Journal of Clinical Microbiology, vol. 36, No. 9, pp. 2772-2774, Sep. 1998.

Alexander et al. (1998) "Purification of total RNA from human stool samples," Digestive Diseases and Sciences, 43:2652-2658.

Barry et al. (1993) "Identification of Deoxyribonuclease 11 as an Endonucleas Involved in Apoptosis," Archives of Biochemistry and Biophysics, 300(1):440-450.

Boehm et al. (1997) "Deletion Analysis at the DEL-27, APC and MTS-1 Loci in Bladder Cancer: LOH at the DEL-27 Locus on 5p13-12 is a Prognostic Marker of Tumor Progression," Int. J. Cancer, 74:291-295.

Brisco et al. (1991) "Detection and Quantitation of Neoplastic Cells in Acute Lymphoblastic Leukaemia by Use of the Polymerase Chain Reaction," British Journal of Haematology, 79:211-217.

Brisco et al. (1994) "Outcome Prediction in Childhood Acute Lymphoblastic Leukaemia by Molecular Quantification of Residual Disease at the End of Induction," The Lancet, 343(8891):196-200.

Everett et al. (1999) "Identification of nine species of the Chlamydiaceae Using PCR-RFLP," 49(2):803-813.

Halford et al. (1999) "The Inherent Quantitative Capacity of the Reverse Transcription-Polymerase Chain Reaction," Analytical Biochemistry, 266(2):181-191.

Hickman et al. (1994) "Apoptosis and cancer chemotherapy," Phil. Trans R. Soc. Lond., 345:319-325.

Hoss et al. (1992) "Excrement Analysis by PCR" Scientific Correspondence pp. 199.

Jeffreys et al. (1995) "Mutation Processes at Human Minisatellites," Electrophoresis, 16(1):1577-1585.

Kawakami et al. (2000) "Hypermethylated APC DNC in Plasma and Prognosis of Patients with Esophageal Adenocarcinoma," Journal of the National Cancer Institute, 92(22):1805-1811.

Ko et al. (1999) "Genomic Instability and Alterations in Apc, Mcc and Dcc in Hong Kong Patients with Colorectal Carcinoma, " Int. J. Cancer Ped. Oncol, 84:404-409.

Li et al. (1988) "Amplification and Analysis of DNA Sequences in Single Human Sperm and Diploid Cells," Nature, 335(6189):414-417.

Lizardi et al. (1998) "Mutation Detection and Single-Molecule Counting Using Isothermal Rollig-Circle Amplification," Nature Genetics, 19(3):225-232.

Loughlin et al. (2002) "Association of the interleukin-1 gene cluster on chromosome 2q13 with knee osteoarthritis," Arthritis & Rheumatism, 46(6):1519-1527.

Marras et al. (1999) "Multiplex Detection of Single-Nucleotide Variations Using Molecular Beacons," Genetic Analysis: Biomolecular Engineering, 14:151-156.

Monckton et al. (1991) "Minisatellite 'Isoallele' Discrimination in Pseudohomozygotes by Single Molecule PCR and Variant Repeat Mapping," Genomics, 11:465-467.

Morrissey et al. (1989) "Nucleic Acid Hybridization Assays Employing dA-Tailed Capture Probes. Single Capture Methods," Mol. and Cell. Probes, 3(2):189-207.

Mulcahy et al. (1999) "Diagnosis of pancreatico-biliary malignancy: detection of gene mutations in plasma and stool." Ann Oncol.10 Suppl 4:114-7.

Navidi et al. (1991) "Using PCR in Preimplantation Genetic Disease Diagnosis," Human Reproduction, 6(6):836-849.

Parsons et al. (1995) "Mismatch Repair Deficiency in Phenotypically Normal Human Cells," Science, 268(5211):738-740.

Piatek et al. (1998) "Molecular Beacon Sequence Analysis for Detecting Drug Resistance in Mycobacterium Tuberculosis," Nature Biotechnology, 16(4):359-363.

Ruano et al. (1990) "Haplotype of Multiple Polymorphisms Resolved by Enzymatic Amplification of Single DNA Molecules," Proc. Natl. Acad. Sci. USA, 87(16):6296-6300.

Samowitz et al. (1999) "BAT-26 and BAT-40 Instability in Colorectal Adenomas and Carcinomas and Germline Polymorphisms" American Journal of Pathology 154:1637-1641.

Schmitt et al. (1994) "High Sensitive DNA Typing Approaches for Analysis of Forensic Evidence: Comparison of Nested Variable Number of Tandem Repeats (VNTR) Amplification and a Short Tandem Repeats (STR) Polymorphism," Forensice Science International, 66(2):129-141.

Sidransky et al. (1992) "Clonal Expansion of p53 Mutant Cells is Associated with Brain Tumour Progression," Nature, 355(6363):846-847.

Sykes et al. (1992) "Quantitation of targets for PCR by use of limiting dilution" Biotechniques. 13(3):444-9.

Tyagi et al. (1996) "Molecular Beacons: Probes that Fluoresce upon Hybridization," Nature Biotechnology, 14(3):303-308.

Tyagi et al. (1998) "Multicolor Molecular Beacons for allele discrimination," Nature Biotechnology, 16(1):49-53.

Vet et al. (1999) "Multiplex Detection of Four Pathogenic Retroviruses Using Molecular Beacons," Proc. Natl. Acad. Sci. USA, 96(11):6394-6399.

Whitcombe et al. (1999) "Detection of PCR Products Using Self-Probing Amplicons and Fluorescence," Nature Biotechnology, 17:804-807.

Zhang et al. (1992) "Whole Genome Amplification from a Single Cell: Implications for Genetic Analysis," Proc. Natl. Acad. Sci. USA, 89:5847-5851.

Owens et al. (1995) "Overexpression of the Focal Adhesion Kinase (p125FAK) in Invasive Human Tumors," Cancer Research, 55(13):2752-2755.

Pogue-Geile et al. (1991) "Ribosomal protein genes are overexpressed in colorectal cancer: isolation of a cDNA clone encoding the human S3 ribosomal protein," 11(8):3842-3849.

* cited by examiner

200bp
AMPLIFICATIONS
33 CYCLES

| LANE | Q# | SAMPLE TYPE | SAMPLE NUMBER | GRADE |
|---|---|---|---|---|
| 1 | 7903.8 | ABNORMAL | 1 | A |
| 2 | 5627.4 | ABNORMAL | 2 | A |
| 3 | 8809.11 | ABNORMAL | 3 | A |
| 4 | 5421.94 | ABNORMAL | 4 | A |
| 5 | 1838.07 | POSITIVE CONTROL | | B |
| 6 | -549.23 | NORMAL | 5 | C |
| 7 | -715 | NORMAL | 6 | C |
| 8 | -1605.13 | NORMAL | 7 | C |
| 9 | -824.73 | NORMAL | 8 | C |
| 10 | 259.77 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

200bp
AMPLIFICATIONS
35 CYCLES

| LANE | Q# | SAMPLE TYPE | SAMPLE NUMBER | GRADE |
|---|---|---|---|---|
| 1 | 10851.04 | ABNORMAL | 1 | A |
| 2 | 8862.34 | ABNORMAL | 2 | A |
| 3 | 9777.85 | ABNORMAL | 3 | A |
| 4 | 6874.28 | ABNORMAL | 4 | A |
| 5 | 2392.07 | POSITIVE CONTROL | | B |
| 6 | 3080.62 | NORMAL | 5 | B |
| 7 | 813.45 | NORMAL | 6 | C |
| 8 | -720.04 | NORMAL | 7 | C |
| 9 | -442.2 | NORMAL | 8 | C |
| 10 | 1353.86 | NORMAL | 9 | B |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >5000
B= 1000-5000
C= <1000

200bp
AMPLIFICATIONS
34 CYCLES

| LANE | Q# | SAMPLE TYPE | SAMPLE NUMBER | GRADE |
|---|---|---|---|---|
| 1 | 8428.34 | ABNORMAL | 1 | A |
| 2 | 4917.31 | ABNORMAL | 2 | A |
| 3 | 7742.22 | ABNORMAL | 3 | A |
| 4 | 3049.85 | ABNORMAL | 4 | A |
| 5 | 409.5 | POSITIVE CONTROL | | B |
| 6 | -682.75 | NORMAL | 5 | C |
| 7 | -781.09 | NORMAL | 6 | C |
| 8 | -1099.28 | NORMAL | 7 | C |
| 9 | -1015.39 | NORMAL | 8 | C |
| 10 | 359.74 | NORMAL | 9 | B |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >750
B= 250-750
C= <250

200bp
AMPLIFICATIONS
33 CYCLES

| LANE | Q# | SAMPLE TYPE | SAMPLE NUMBER | GRADE |
|---|---|---|---|---|
| 1 | 7879.15 | ABNORMAL | 1 | A |
| 2 | 4079.09 | ABNORMAL | 2 | A |
| 3 | 7995.95 | ABNORMAL | 3 | A |
| 4 | 2600.3 | ABNORMAL | 4 | A |
| 5 | 1698.19 | POSITIVE CONTROL | | B |
| 6 | -405.32 | NORMAL | 5 | C |
| 7 | -466.15 | NORMAL | 6 | C |
| 8 | -1046.47 | NORMAL | 7 | C |
| 9 | -764.83 | NORMAL | 8 | C |
| 10 | 105.05 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

200bp
AMPLIFICATIONS
34 CYCLES

| LANE | Q# | SAMPLE TYPE | SAMPLE NUMBER | GRADE |
|---|---|---|---|---|
| 1 | 7852.95 | ABNORMAL | 1 | A |
| 2 | 4797.07 | ABNORMAL | 2 | A |
| 3 | 8543.47 | ABNORMAL | 3 | A |
| 4 | 3597.23 | ABNORMAL | 4 | A |
| 5 | 943.84 | POSITIVE CONTROL | | B |
| 6 | -296.7 | NORMAL | 5 | C |
| 7 | -5.48 | NORMAL | 6 | C |
| 8 | -896.94 | NORMAL | 7 | C |
| 9 | -196.87 | NORMAL | 8 | C |
| 10 | 414.81 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

200bp
AMPLIFICATIONS
34 CYCLES

| LANE | Q# | SAMPLE TYPE | SAMPLE NUMBER | GRADE |
|---|---|---|---|---|
| 1 | 7660.6 | ABNORMAL | 1 | A |
| 2 | 7032.89 | ABNORMAL | 2 | A |
| 3 | 8364.31 | ABNORMAL | 3 | A |
| 4 | 6892.04 | ABNORMAL | 4 | A |
| 5 | 4883.47 | POSITIVE CONTROL | | A |
| 6 | 1934.67 | NORMAL | 5 | B |
| 7 | 1380.84 | NORMAL | 6 | B |
| 8 | -964.17 | NORMAL | 7 | C |
| 9 | 1729.51 | NORMAL | 8 | B |
| 10 | 2221.69 | NORMAL | 9 | B |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >5000
B= 1000-5000
C= <1000

200bp
AMPLIFICATIONS
33 CYCLES

| LANE | Q# | SAMPLE TYPE | SAMPLE NUMBER | GRADE |
|---|---|---|---|---|
| 1 | 8519.13 | ABNORMAL | 1 | A |
| 2 | 5745.19 | ABNORMAL | 2 | A |
| 3 | 9765.65 | ABNORMAL | 3 | A |
| 4 | 4153.79 | ABNORMAL | 4 | A |
| 5 | 1869.33 | POSITIVE CONTROL | | B |
| 6 | 418.37 | NORMAL | 5 | C |
| 7 | 405.91 | NORMAL | 6 | C |
| 8 | -258.08 | NORMAL | 7 | C |
| 9 | 141.64 | NORMAL | 8 | C |
| 10 | 450.78 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

| 1.8kb AMPLIFICATIONS 36 CYCLES | | |
|---|---|---|
| LANE | Q# | SAMPLE |
| 1 | | NEG CONTROL |
| 2 | 102.935 | ABNORMAL |
| 3 | 260.645 | ABNORMAL |
| 4 | 0.075 | NORMAL |
| 5 | 48.305 | ABNORMAL |
| 6 | 0.045 | NORMAL |
| 7 | 18.575 | NORMAL |
| 8 | | NEG CONTROL |
| 9 | | NEG CONTROL |
| 10 | 75 | 75 |
| 11 | 125 | 125 |
| 12 | 250 | 250 |
| 13 | 500 | 500 |
| 14 | 1000 | 1000 |

ABNORMAL / NORMAL CUTOFF  40

| 1.8kb<br>AMPLIFICATIONS<br>38 CYCLES | | |
|---|---|---|
| LANE | Q# | SAMPLE |
| 1 | | NEG CONTROL |
| 2 | 81.84 | ABNORMAL |
| 3 | 91.515 | ABNORMAL |
| 4 | 0.04 | NORMAL |
| 5 | 24.86 | ABNORMAL |
| 6 | 0.88 | NORMAL |
| 7 | 17.25 | NORMAL |
| 8 | | NEG CONTROL |
| 9 | | NEG CONTROL |
| 10 | 75 | 75 |
| 11 | 125 | 125 |
| 12 | 250 | 250 |
| 13 | 500 | 500 |
| 14 | 1000 | 1000 |

ABNORMAL / NORMAL CUTOFF  20

| 1.8kb AMPLIFICATIONS 40 CYCLES | | |
|---|---|---|
| LANE | Q# | SAMPLE |
| 1 | | NEG CONTROL |
| 2 | 70.72 | ABNORMAL |
| 3 | 92.78 | ABNORMAL |
| 4 | 96.76 | ABNORMAL |
| 5 | 0.00 | NORMAL |
| 6 | 29.85 | ABNORMAL |
| 7 | 0.00 | NORMAL |
| 8 | 2.00 | NORMAL |
| 9 | | NEG CONTROL |
| 10 | | NEG CONTROL |
| 11 | 75 | 75 |
| 12 | 125 | 125 |
| 13 | 250 | 250 |
| 14 | 500 | 500 |
| 15 | 1000 | 1000 |
| 16 | 2000 | 2000 |

ABNORMAL / NORMAL CUTOFF  10

METHODS FOR DISEASE DETECTION

The present application is a continuation of U.S. Ser. No. 10/434,482, filed May 7, 2003, which is a continuation of U.S. Ser. No. 09/455,950, filed Dec. 7, 1999, issued as U.S. Pat. No. 6,586,177 on Jul. 1, 2003, which claims priority to and the benefit of U.S. Provisional patent application Ser. No. 60/152,847, filed Sep. 8, 1999, the entire disclosures of which are incorporated herein by reference.

BACKGROUND OF THE INVENTION

Many diseases are associated with genomic instability. That is, a disruption in genomic stability, such as a mutation, has been linked to the onset or progression of certain diseases. Accordingly, various aspects of genomic instability have been proposed as reliable markers for disease. For example, mutations in the BRCA genes have been proposed as markers for breast cancer, and mutations in the p53 cell cycle regulator gene have been associated with numerous cancers, especially colorectal cancer. It has been suggested that specific mutations might be a basis for molecular screening assays for the early stages of certain types of cancer. See, e.g., Sidransky, et al., Science, 256: 102-105 (1992).

The search for genomic disease markers has been especially intense in the area of cancer detection. Cancer is characterized by uncontrolled cell growth which can be associated with one or more genetic mutations. Such mutations can cause the affected cells to avoid cell death. For example, a mutation in a tumor suppressor gene can cause cells to avoid apoptosis—a type of cell death thought to be under direct genetic control. During apoptosis, cells lose their membranes, the cytoplasm condenses, and nuclear chromatin is split into oligonucleotide fragments of characteristically short length. In fact, those characteristic DNA cleavage patterns have been proposed as an assay for apoptosis.

Attempts have been made to identify and use nucleic acid markers that are indicative of cancer. However, even when such markers are found, using them to screen patient samples, especially heterogeneous samples, has proven unsuccessful either due to an inability to obtain sufficient sample material, or due to the low sensitivity that results from measuring only a single marker. Simply obtaining an adequate amount of human DNA from one type of heterogeneous sample, stool, has proven difficult. See Villa, et al., Gastroenterol., 110: 1346-1353 (1996) (reporting that only 44.7% of all stool specimens, and only 32.6% of stools from healthy individuals produced sufficient DNA for mutation analysis). Other reports in which adequate DNA has been obtained have reported low sensitivity in identifying a patient's disease status based upon a single cancer-associated mutation. See Eguchi, et al., Cancer, 77: 1707-1710 (1996) (using a p53 mutation as a marker for cancer).

Investigators have attempted to analyze mutations in DNA of tumor cells shed into luminal areas, such as the colon, bile ducts, blood vessels and the like. Such attempts have only been successful when there is a known mutation and a relatively high concentration of cellular material has been found. See e.g., Mulcahy, et al., Ann. Oncol. 10 Suppl 4:114-117 (1999). No attempts have been made to correlate disease status with DNA integrity in shed cellular material.

SUMMARY OF THE INVENTION

The present invention provides that the integrity of nucleic acids in biological samples comprising shed cellular material is an indicator of the disease status of the patient from whom the sample was obtained. According to the invention, certain tissue or body fluid samples, especially those described below, contain debris from cells that have been shed from surrounding organs or tissue. In healthy patients, such debris is the result of apoptosis as part of the normal cell cycle. Apoptosis reduces nucleic acid integrity, so that only small-fragment nucleic acids exist in exfoliated cellular debris in healthy individuals. To the contrary, in diseases such as cancer in which cell cycle mechanisms are destroyed or impaired, cellular debris comprises high-integrity nucleic acids (i.e., nucleic acids that have not been degraded by apoptosis). Thus, methods of the invention comprise using nucleic acid integrity as a measure of patient disease status. Integrity can be measured by any convenient means. Preferred means include the amount of nucleic acid in a sample, the length of nucleic acids in a sample, or the molecular weight of nucleic acids in a sample.

The invention provides methods for detecting disease in a patient based upon the integrity of patient nucleic acids present in a specimen or sample obtained from the patient. According to methods of the invention, a tissue or body fluid specimen containing sloughed cellular debris obtained from a patient having a disease contains an amount of intact nucleic acid that is greater than would be expected in such a specimen obtained from a healthy patient. Thus, a measure of intact nucleic acid in a patient sample is indicative of the overall disease status of the patient. As used herein, "intact" refers to nucleic acids that are longer than those expected to be present as a result of apoptosis. The invention is equally applicable to human and to veterinary uses. Accordingly, "patient" as defined herein means humans or other animals.

A healthy patient generally produces cellular debris through normal apoptotic degradation, resulting in relatively short nucleic acid fragments in samples derived from luminal tissue and fluids. Patients having a disease generally produce cells and cellular debris, a proportion of which has avoided normal cell cycle regulation, resulting in relatively long, intact nucleic acid fragments. Without being held to theory, the present invention takes advantage of this and other insights concerning the ways in which cells respond to diseases, especially diseases associated with genetic abnormalities (either induced or inherited). As a result, it has been discovered that the disease status of a patient is determined by analysis of patient nucleic acids produced in specimens obtained from the patient. Most preferably, such specimens are those most likely to contain sloughed cellular debris. Such specimens include, but are not limited to, stool, blood serum or plasma, sputum, pus, colostrum, and others. In diseases, such as cancer, in which genomic instabilities or abnormalities have interfered with normal cell cycle regulation, specimens such as those identified above contain relatively intact nucleic acid fragments. The presence of such fragments is a general diagnostic screen for disease.

Accordingly, methods of the invention comprise screening a patient for disease by analysis of the integrity of nucleic acids in a tissue or body fluid specimen obtained from the patient. Preferred specimens include those comprising shed cells or cellular debris. Thus, highly-preferred specimens are those not containing an abundance of intact (non-exfoliated) cells. Such preferred specimens comprise stool, sputum, urine, bile, pancreatic juice, and blood serum or plasma, all of which contain shed cells or cellular debris. Methods of the invention are especially useful as screens for cancer. Cancer is a disease thought to be associated with genomic instabilities, and specifically with the loss of control over the normal cell cycle. Thus, tumor cells are typically intact and routinely are shed into, for example, stool, sputum, urine, bile, pancreatic juice, and blood. Such shed cells and cellular debris contain higher integrity nucleic acids compared to those found in specimens obtained from a healthy patient. There are numerous ways in which the integrity of nucleic acids in a patient specimen are measured as a screen for disease.

In a preferred embodiment, nucleic acid integrity is measured by the ability to amplify nucleic acids in a sample. Thus, a preferred method comprises conducting in a tissue or body fluid sample an amplification reaction using as a template a nucleic acid locus suspected to be in the sample. If the amount of amplification product (amplicon) is greater than the amount of amplicon expected to be present in a normal sample (e.g., one not having the disease being screened), the sample is determined to be positive. In some cases, the presence of any amplification product is sufficient to justify a positive screen for disease. It is preferable that, in the case of DNA, the amplification reaction is a polymerase chain reaction (PCR) or, in the case of RNA, that the amplification reaction is reverse transcriptase PCR. Primers are designed to amplify the locus or loci chosen for analysis. For purposes of the invention a "genomic locus" is any genetic element, including but not limited to a coding region of a gene, a non-coding nucleic acid region, a regulatory element of a gene, an intron or RNA. It is not required that the target genomic loci be associated with any specific disease, as an increase in amplifiable nucleic acid is itself diagnostic.

In one preferred embodiment, the presence of a single high molecular weight amplicon is a positive screen. Preferably, a fragment of about 1.3 Kb or greater is measured as an indicator of high integrity nucleic acids in the patient sample.

In a highly-preferred embodiment, a profile of amplification products across a range of nucleic acid fragments of different lengths is produced. In a preferred embodiment, a series of amplification reactions is conducted at a single genomic locus, each reaction being designed to amplify a fragment of unique length. If detectable amplicon is produced in each reaction, or in a number of reactions greater than expected in a sample obtained from a healthy patient, the sample is determined to be positive. For example, attempts are made to amplify fragments of 200 bp, 400 bp, 800 bp, 1.3 Kb, 1.8 Kb, and 2.4 Kb at the same genomic locus. In a sample obtained from a healthy individual (a "normal" sample), it would be expected that little or no amplification product is observed, especially when the longer portions of the locus are used as the template. To the contrary, at least some proportion of cells and cellular debris in a sample obtained from a diseased patient will contain intact fragments.

In another embodiment, a profile of amplification products across a range of nucleic acid fragments of different lengths is produced by a series of amplification reactions conducted on a series of different genomic loci, each reaction being designed to amplify a fragment of unique length. If detectable amplicon is produced in each reaction, or in a number of reactions greater than expected in a sample obtained from a patient not having the disease being screened, the sample is determined to be positive.

According to methods of the invention, normal samples do not produce significant amounts of detectable amplicon at any length significantly greater than the typical apoptotic fragment (about 175 bp). Accordingly, whether primers are spaced to amplify fragments of only one length at a given genomic locus, or whether a series of amplifications at the locus are conducted, differences are readily observable between normal and diseased samples.

As detailed below, methods of the invention are useful to detect disease, preferably cancer or precancer, in biological samples comprising shed cells or cellular debris. For example, the presence in a patient stool sample of amounts of nucleic acid, preferably DNA, above a predetermined threshold for healthy patients is indicative that the patient has cancer. Follow-up analysis is used to determine where the disease resides. However, the general disease screen is effective independent of the locus of the disease and the specimen taken for analysis. Thus, while the analysis of nucleic acids in stool is predictive of disease generally, it does not necessarily indicate that the disease is of gastrointestinal origin. However, follow-up screening based, for example, on mutational analysis, is adequate to identify the locus of disease. Numerous mutational analyses are known in the art and include, for example, U.S. Pat. No. 5,670,325, incorporated by reference herein.

In an alternative embodiment, screening of patient samples by detecting amounts of nucleic acid in the sample is combined with an assay for apoptotic cell activity. Such assays may be combined with detecting amounts of nucleic acid in a patient sample as a screen for disease status. A positive screen is one that produces both: (1) an amount of nucleic acid that is greater than the amount expected to be present in a normal sample (e.g., one not having the disease being screened), and (2) an amount of apoptotic cell activity that is less than that expected to be present in a normal sample. In a highly preferred embodiment, methods of the invention comprise analyzing a plurality of genomic loci to determine an amount of amplifiable nucleic acid present at each locus. Analysis across multiple loci using methods of the invention may increase the sensitivity of the screening assay.

As will be exemplified in detail below, methods of the invention comprise screening a biological sample for an abnormality in a nucleic acid by conducting an amplification reaction using as a template a nucleic acid suspected or expected to be in the sample; determining an amount of amplification product obtained; comparing the amount of amplicon obtained to a standard amount of amplification product; and identifying a sample as having an abnormality in a nucleic acid if the amount of amplification product differs from the standard amount. In a preferred embodiment, a standard amount of amplification product is determined by amplification of a locus, or portion thereof, being screened (e.g., an intact, wild-type nucleic acid) in a known normal sample (one obtained from an individual known not to have the disease being screened). Also in preferred embodiments, a standard amount is determined by reference to the art. In certain embodiments of the invention, the standard amount is essentially no detectable amplicon due to the lack of high-integrity nucleic acids in the sample. Accordingly, any detectable amplicon in a patient sample is indicative of a positive screen. That is the case especially when a large (e.g., 1.8 Kb or 2.4 Kb) fragment is being screened. Finally, the standard amount can be a molecular weight marker on, for example, an electrophoretic gel.

In a preferred embodiment of the invention, the sample is prepared from a specimen selected from the group consisting of stool, sputum, blood, urine, cerebrospinal fluid, seminal fluid, saliva, breast nipple aspirate, and biopsy tissue. However, any tissue or body fluid specimen may be used according to methods of the invention. Especially preferred are samples of luminal fluid because such samples are generally free of intact, healthy cells. Such samples include blood, urine, bile, pancreatic juice, stool, sputum, pus, and the like.

Also in a preferred embodiment, the nucleic acid or nucleic acids being interrogated is (are) DNA. In a more particular embodiment, the nucleic acid being analyzed is selected from a coding region of a gene, or portion thereof, a noncoding nucleic acid region, or portion thereof, a regulatory element of a gene or a portion thereof, and an unidentified fragment of genomic DNA. Also in a preferred embodiment, the nucleic acid being interrogated is RNA. As is appreciated by the skilled artisan, any genomic locus is amenable to screening according to the invention. The particular locus or loci chosen for analysis depends, in part, on the disease being screened, and the convenience of the investigator. It is not necessary that the locus or loci chosen for analysis be correlated with any specific disease because methods of the invention contemplate measuring either the total nucleic acid in a sample or amplifiable nucleic acid in a sample as an indicator of overall disease status or the presence and/or extent of apoptosis in the sample. However, disease-associated loci (those in which a mutation is indicative, causative, or otherwise evidence of a disease) can be used. Preferred disease-associated loci include p53, apc, MSH-2, dcc, scr, c-myc, B-catnenin, mlh-1, pms-1, pms-2, pol-delta, and bax.

The amount of amplification product may be determined by any suitable or convenient means. Preferably, the amount of amplification product is determined by gel electrophoresis. Labels, such as fluorescent or radioactive labels, may be used.

The amounts of amplification product produced may be compared to standard amounts by any suitable or convenient means, including, but not limited to visual comparison, machine-driven optical comparison, densitometry, mass spectroscopy, hybrid capture, and other known means. The amplification reaction itself can be any means for amplifying nucleic acid, including, but not limited to PCR, RT-PCR, OLA, rolling circle, single base extension, and others known in the art. The amplification product can also be measured by signal amplification techniques, such as branch chain amplification (Chiron). Methods of the invention are useful with any platform for the identification, amplification, sequencing, or other manipulation of nucleic acids. For example, methods of the invention can be applied to ligase chain reaction, strand displacement (Becton-Dickinson), and others.

Also in a preferred embodiment of the invention, a series of amplification reactions is conducted on a single genomic locus. Each amplification reaction in the series is designed to amplify a fragment of a different length. In a preferred embodiment, the target fragment lengths are 200 bp, 400 bp, 800 bp, 1.3 Kb, 1.8 Kb, and 2.4 Kb. Primers for amplification are designed according to knowledge in the art in order to amplify template, if present, of the desired length at the desired locus. A positive screen is one that produces amplicon in at least one, and preferably at least two of the series of amplification reactions. As noted above, a normal sample which has undergone or which is undergoing apoptosis typically contains little or no fragments of significant length. Thus, a series of amplification reactions targeting fragments from about 200 bp to about 2.4 Kb and longer reveals samples that contain nucleic acids that have avoided apoptosis as evidenced by the amplification of large fragments.

Preferred methods of the invention also comprise conducting amplification reactions on a series of different genomic loci. Preferably, from about 2 to about 7 loci are used. However, the precise number of interrogated loci is determined by the individual investigator based upon the disease to be detected or based upon convenience. According to methods of the invention, primers are designed to amplify nucleic acid (preferably DNA) at each of the chosen loci. A sample in which at least one locus, preferably at least two loci, and most preferably at least three loci produce detectable amplification product is considered a positive sample. The lengths of fragments to be amplified in this assay may be varied, but are preferably at least about 180 bp each in length. It is not necessary that the same length fragments be amplified at each of the chosen loci.

Methods of the invention also comprise conducting a series of amplification reactions at a series of different genomic loci. Each amplification reaction in the series is designed to amplify a fragment of a different length. Preferably, from about 2 to about 7 amplification reactions on about 2 to about 7 loci are used. However, the precise number of interrogated loci is determined by the individual investigator based upon the disease to be detected or based upon convenience. In a preferred embodiment, the target fragment lengths are 200 bp, 400 bp, 800 bp, 1.3 Kb, 1.8 Kb, and 2.4 Kb. Primers for amplification are designed according to knowledge in the art in order to amplify template if present. It is preferred, but not necessary, that the same length fragments be amplified at each of the chosen loci. A positive screen is one that produces amplicon in at least one, and preferably at least two of the series of amplification reactions and in which at least one locus, preferably at least two loci, and most preferably at least three loci produce detectable amplification product. As noted above, a normal sample which has undergone or which is undergoing apoptosis typically contains little or no fragments of significant length. Thus, a series of amplification reactions targeting fragments from about 200 bp to about 2.4 Kb and longer reveals samples that contain nucleic acids that have avoided apoptosis as evidenced by the amplification of large fragments.

Methods of the invention may also be used to assess the integrity of DNA in a biological sample. Such methods comprise conducting an amplification reaction using at least two loci suspected to be in the sample as templates; determining which loci produce detectable amplicon; and assessing the integrity of DNA in the sample as a function of the number of loci producing amplicon. The integrity of DNA in the sample is high when amplicon is produced in one or more of the amplification reactions. This method is especially useful for determining whether a heterogeneous sample has sufficient nucleic acid for measurement. Accordingly, such methods are used to screen or to "qualify" samples for further analysis (e.g., genetic, biochemical, cytological, or other analyses).

Methods of the invention may also be used to assess fetal abnormalities by conducting amplification reactions on nucleic acids in maternal blood. Just as described above, the ability to amplify significant amounts of nucleic acid is an indicator of a genomic instability. A baseline for comparison of the extent of nucleic acid amplification can be amounts of nucleic acids from known normal samples. The amount of amplification obtained from fetal samples is placed on a continuum, and the investigator must analyze any given sample in terms of the amount of fetal nucleic acid produced in various disease states and in normal samples.

Methods of the invention are useful as diagnostic screening methods. Often it is desirable to perform follow-up testing on a patient in order to confirm a suspected disease state. Such follow-up procedures are determined based upon the disease state being interrogated. For example, a colonoscopy may be suggested in a case in which a stool sample is positively screened according to methods of the invention. Such follow-up procedures are contemplated herein as part of the invention.

Methods of the invention are useful as screens for a wide range of disease states. In addition to colon cancers and adenomas, methods of the invention are useful to screen for other diseases, for example, as screens for lymphomas, or stomach, lung, liver, pancreas, prostate, kidney, testicular, bladder, uterus, or ovarian cancers or adenomas. In addition to cancer, methods of the invention are useful, for example, as screens for diseases such as inflammatory bowel syndrome, inflammatory bowel disease, Crohn's disease, and others in which a genomic instability is thought to play a role. Methods of the invention are especially useful as screens for any disease that impairs the proper function of the gastrointestinal system; most especially diseases of the colon. Methods of the invention are also useful to screen for apoptosis in a cellular sample. The profile of amplifiable DNA in a sample is correlated with proteins that have been associated with disease. For example up regulation of the apoptosis protein, survivin, is correlated with increased amounts of amplifiable DNA, as is the Ras oncogene, as well as other oncogenes and their gene products.

Methods of the invention are also useful as assays for apoptosis. The presence of high-integrity fragments or large quantities of nucleic acids in a sample indicates that the sample was derived from cells that did not proceed through apoptosis. The absence of such fragments or quantities indicates that cells that contributed to the sample did undergo apoptosis. Accordingly, an apoptotic activity assay of the invention, either alone or in combination with other assays for genomic instability, are useful as screens for disease.

Finally, methods of the invention can be carried out by hybrid capture. For example, hybrid capture and subsequent analysis of the captured fragments can be used to determine the nucleic acid integrity of a sample.

The invention also provides a profile of nucleic acid fragments indicative of disease. A preferred profile is obtained through methods described above. Preferred profiles comprise nucleic acids having between about 200 bp and about 2.4 Kb obtained in a patient sample comprising cellular debris according to methods described herein. A highly preferred profile contains at least one nucleic acid of at least 1.3 Kb.

Other objects and advantages of the invention are apparent upon consideration of the following drawings and detailed description thereof.

DETAILED DESCRIPTION OF THE INVENTION

The invention provides methods for the analysis of biological samples. Methods of the invention provide diagnostically-relevant information based upon the integrity of nucleic acids in a biological sample. Normal biological samples (those not having indicia of the disease being screened), especially those comprising luminal tissue and/or fluid, typically comprise a majority of short-fragment, low-integrity nucleic acids (especially DNA) which are the result of degradation by apoptosis. When a mutation has caused genomic instability, the normal cell cycle may be disrupted and apoptotic degradation may not occur at the rate expected in a normal sample. Methods of the invention screen for such disruptions.

Accordingly, preferred methods of the invention comprise determining an amount of amplifiable nucleic acid in a biological sample, and determining whether that amount is consistent with an amount expected in a normal sample. In many biological samples, especially heterogeneous samples, there may be no detectable amplification product. That is especially true when longer fragments are used as templates for amplification. Generally, the probability that any given set of PCR primers will amplify a DNA fragment having a length exceeding the primer distance is expressed as % of Fragments Amplified=$(FL-PD)/(FL+PD)$ wherein FL is fragment length (in base pairs) and PD is primer distance (in base pairs). This equation assumes that sample DNA fragment lengths are uniformly distributed (i.e., there is no favored locus at which breaks occur).

Figure 12:
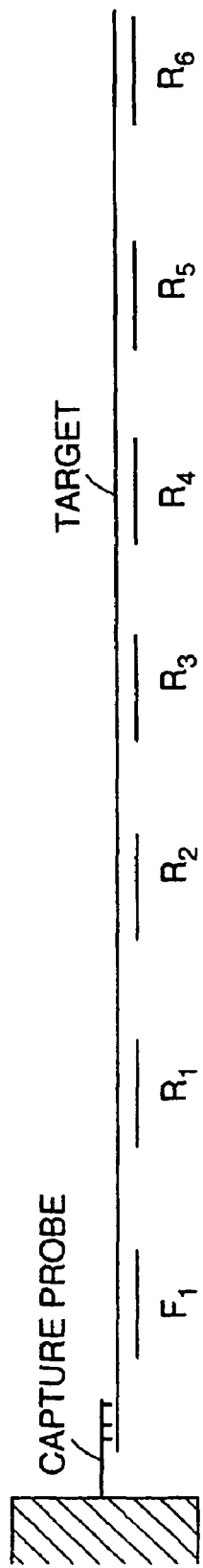
FIG. 12 shows a schematic representation of the placement of the primers for amplification in a method of the present invention. In this method, a single forward primer, $F_1$, is used in conjunction with a series of reverse primers, $R_1$ to $R_6$, chosen to amplify progressively longer portions of the target.

In a preferred embodiment, methods of the invention comprise amplifying sequences of different length in a sample, if present, in order to generate a profile of amplification products indicative of disease or the propensity for disease. In a preferred method, a sample is exposed to a set of PCR primers comprising a single forward primer, which may be a capture probe used to capture target fragments, and a plurality of downstream reverse primers which hybridize to portions of a contiguous sequence (if present) in the sample. Amplifications using these primers will result in a series of amplification products, each having a different length, if the contiguous target sequence is present in the sample. The length of the amplification products are determined by the spacings between the forward primer and each of the downstream reverse primers. An example is shown in FIG. 12, which is a schematic representation showing placement of the primers for amplification.

If the target sequence, or a portion of it, is present in the sample, amplification will result in a series of fragments the length of which is dictated by the spacing of the primers. According to the principles adduced above, a sample from a diseased patient will produce a profile of amplification products in the assay described above that differs from the profile obtained from a sample containing the smaller fragments expected to be produced as a result of normal apoptosis. In a preferred embodiment, the forward primer is designed to hybridize about 200 bp upstream of the first reverse primer, and about 2.3 Kb upstream of the last reverse primer. Other reverse primers are designed to hybridize at various locations between the first and last reverse primers. Preferred intervals between the forward primer and the various reverse primers are 200 bp ($F_1$-$R_1$), 400 bp ($F_1$-$R_2$), 800 bp ($F_1$-$R_3$), 1.3 Kb, ($F_1$-$R_4$), 1.8 Kb ($F_1$-$R_5$), and 2.3 Kb ($F_1$-$R_6$). The number and spacing of reverse primers is chosen at the convenience of the skilled artisan.

Also in a preferred embodiment, a hybrid capture probe is used to anchor a target sequence, preferably on a solid support (e.g., beads). A plurality of probes are then placed at various distances downstream of the capture probe. Those probes can be pairs of forward and reverse primers as discussed above, or they can be signal amplification probes, such as those used in Ligase Chain Reaction (LCR), and others used in the identification of sequences. The plurality of probes hybridize along the length of a target fragment if the target is present in the sample. Thus, by interrogating samples for the presence of the probes, one can determine the integrity of sequences present in the sample. This can be done in numerous ways, including, but not limited to, hybrid capture, PCR, LCR, strand displacement, branched chain, or other assays known in the are that incorporate hybrid probes or primers in order to identify or quantitate sequence. A sample containing intact (high integrity) nucleic acids represents a positive screen according to the invention. In one embodiment, sample is placed into wells (e.g., on a 96 well plate) containing support-bound capture probe. The capture probe immobilizes a target sequence, if present in the sample. Probes that hybridize to sequence downstream of the capture probe (downstream probes) are placed into each well, such that each downstream probe is spaced a unique distance apart from the common capture probe, and each well contains only one type of downstream probe. Signal is then generated by, for example, amplification, or by standard ELISA procedure followed by amplification, or by LCR, or other methods mentioned above. The presence of signal in each well indicates the presence of sequence of at least the length between the capture probe and the downstream probe. In an alternative embodiment, each well receives multiple different downstream probes, which may be distinctly labeled, and the presence of label(s) is correlated with the length of sequence presence in the sample.

A sample from a patient having, for example, cancer will produce amplicon between most or all of the primer pairs (depending, inter alia, on the length of the target fragments, on the spacing of the primers, and where on the target the primers are spaced). Such a profile represents a positive screen for disease or the propensity for disease. A sample from a patient who does not have indicia of disease results in little or no amplification product in the assay described above. In a negative screen there may be amplification of small (e.g., 200 bp) fragments but there should be no amplification of larger fragments (i.e., fragments resulting from amplification between the forward primer and spaced-apart reverse primers). In cancer diagnostics, the target fragment may optionally be an oncogene, a tumor suppressor, or any other marker associated with cancer. However, it is not necessary to use cancer-associated markers in methods of the invention, as such methods are based on the general recognition that samples indicative of disease contain a greater amount of intact nucleic acids and a greater amount of long fragment nucleic acids. Accordingly, any convenient target nucleic acid locus may be used in the methods of the invention.

The amplification reactions described above may be conducted according to any suitable or convenient protocol and the fragment size of the resulting amplification products (if any) may be determined by any suitable or convenient means.

Figure 13:
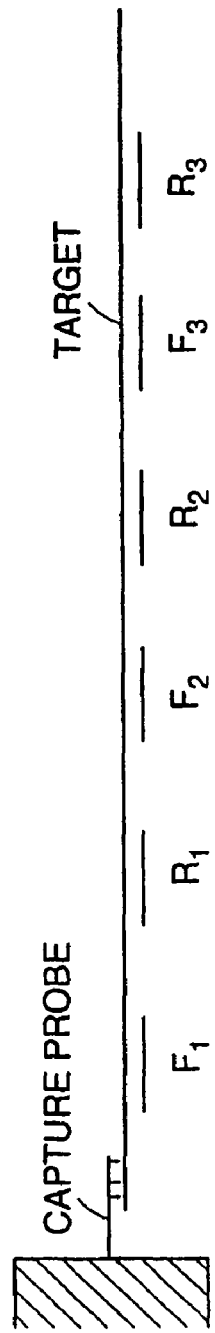
FIG. 13 shows a schematic representation of the placement of the primers for amplification in a method of the present invention. In this method, a series of forward and reverse primer pairs, $(F_1, R_1)$ to $(F_3, R_3)$, are chosen to amplify portions of the target spaced at intervals along the target.

In an alternative embodiment, methods of the invention comprise conducting a series of amplification reactions on a contiguous nucleic acid target fragment, each application reaction comprising one forward primer and one reverse primer, such that pairs of forward and reverse primers are spaced at intervals on a contiguous fragment suspected to be in the sample. An example of this arrangement is shown in FIG. 13. Preferably, the spacings between each forward and reverse primer pair are equivalent. In a positive screen, the assay described above will result in a series of same-size fragments for most if not all of the primer pairs. Such an array of amplification products evidences a contiguous target sequence indicative of disease (see above). A sample from a disease-free patient should produce little or no amplification product, but in any case will not produce the contiguous array of amplification products expected from a sample containing a relatively intact diagnostic target sequence.

Each of the methods described above are based upon the principle that an intact nucleic acid, or a segment of an intact nucleic acid, in a sample is diagnostic. Thus, variations on the methods described above are contemplated. Such variations include the placement of primers, the number of primers used, the target sequence, the method for identifying sequences, and others. For example, in the method depicted in FIG. 13, and described above, it is not necessary that the numbers of forward and reverse primers be equal. A forward primer may, for example, be used to amplify fragments between two reverse primers. Other variations in primer pair placement are within the skill in the art, as are details of the amplification reactions to be conducted. Finally, as represented in FIGS. 12 and 13, capture probes may be used in methods of the invention in order to isolate a chosen target sequence.

The following examples provide further details of methods according to the invention. For purposes of exemplification, the following examples provide details of the use of the method if the present invention in colon cancer detection. Accordingly, while exemplified in the following manner, the invention is not so limited and the skilled artisan will appreciate its wide range of application upon consideration thereof.

Exemplary Method for the Detection of Colon Cancer

The following example relates to screening for colon cancer in voided stool samples. Based upon the principles upon which the invention is based (see above), the same analysis can be performed on other samples, such as those mentioned above, with the same results as shown herein.

For the analysis of stool samples, preferred methods of the invention comprise obtaining at least a cross-sectional or circumferential portion of a voided stool as taught in U.S. Pat. No. 5,741,650, and co-pending, co-owned U.S. patent application Ser. No. 09/059,718, both of which are incorporated by reference herein. While a cross-sectional or circumferential portion of stool is desirable, methods provided herein are conducted on random samples obtained from voided stool, which include smears or scrapings. Once obtained, the stool specimen is homogenized. A preferable buffer for homogenization is one that contains at least 16 mM ethylenediaminetetraacetic acid (EDTA). However, as taught in co-pending, co-owned U.S. patent application Ser. No. 60/122,177, incorporated by reference herein, it has been discovered that the use of at least 150 mM EDTA greatly improves the yield of nucleic acid from stool. Thus, a preferred buffer for stool homogenization comprises phosphate buffered saline, 20-100 mM NaCl or KCl, at least 150 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed. Total DNA is isolated using techniques known in the art.

Screening Assay Protocol

The size of human DNA fragments obtained above can be determined by numerous means. For example, human DNA can be separated using gel electrophoresis. A 3% agarose gel is prepared using techniques known in the art. See Ausubel et. al., Short Protocols in Molecular Biology, John Wiley & Sones, 1195, pgs. 2-23-2-24, incorporated by reference herein. The size of human DNA fragments is then determined by comparison to known standards. Fragments greater than about 200 bp provide a positive screen. While a diagnosis can be made on the basis of the screen alone, patients presenting a positive screen are preferably advised to seek follow-up testing to render a confirmed diagnosis.

A preferred means for determining human DNA fragment length uses PCR. Methods for implementing PCR are well-known. In the present invention, human DNA fragments are amplified using human-specific primers. Amplicon of greater than about 200 bp produced by PCR represents a positive screen. Other amplification reactions and modifications of PCR, such as ligase chain reaction, reverse-phase PCR, Q-PCR, and others may be used to produce detectable levels of amplicon. Amplicon may be detected by coupling to a reporter (e.g. fluorescence, radioisotopes, and the like), by sequencing, by gel electrophoresis, by mass spectrometry, or by any other means known in the art, as long as the length, weight, or other characteristic of the amplicons identifies them by size.

EXAMPLES

Experiments were conducted to determine whether characteristics of amplifiable DNA in stool were predictive of cancer or precancer in patients from whom stools samples were obtained. In the first experiment, the amount of amplifiable DNA was measured in each of several stool samples using PCR amplification to detect DNA fragments in the sample of at least 200 base pairs in length. The second experiment determined the amount of long fragments (greater than 200 base pair) in the same samples, and then determined ratios of long product to short product. The third experiment determined a profile of amplification products with nucleic acid fragment lengths of 200 bp, 400 bp, 800 bp, 1.3 Kb, 1.8 Kb and 2.4 Kb. The fourth and fifth experiments were clinical studies correlating the integrity of nucleic acids in patient stool samples with overall patient disease status.

Example 1

Stool samples were collected from 9 patients who presented with symptoms or a medical history that indicated that a colonoscopy should be performed. Each stool sample was frozen. Immediately after providing a stool sample, each patient was given a colonoscopy in order to determine the patient's disease status. Based upon the colonoscopy results, and subsequent histological analysis of biopsy samples taken during colonoscopy, individuals were placed into one of two groups: normal or abnormal. The abnormal group consisted of patients with cancer or with an adenoma of at least 1 cm in diameter. Based upon these results, 4 of the 9 patients were placed into the abnormal group.

The samples were screened by hybrid capturing human DNA, and determining the amount of amplifiable DNA having at least 200 base pairs. Each frozen stool specimen, weighing from 7-33 grams, was thawed and homogenized in 500 mM Tris, 16 mM EDTA, and 10 mM NaCl, pH 9.0 at a volume, to mass ratio of 3:1. Samples were then rehomogenized in the same buffer to a final volume-to-mass ratio of 20:1, and spun in glass macro beads at 2356×g. The supernatant was collected and treated with SDS and proteinase k. The DNA was then phenol-chloroform extracted and precipitated with alcohol. The precipitate was suspended in 10 mM Tris and 1 mM EDTA (1×TE), pH 7.4. Finally, the DNA was treated with Rnase.

Human DNA was isolated from the precipitate by sequence-specific hybrid capture. Biotynilated probes against portions of the p53, K-ras, and apc genes were used.

The K-ras probe was 5'GTGGAGTATTTGATAGTGTATTAACCTTATGTGTGAC 3' (SEQ ID NO: 1).

There were two apc probes: apc-1309 was 5'TTCCAGCAGTGTCACAGCACCCTAGAACCAAATCCAG 3' (SEQ ID NO: 2), and apc-1378 was 5'CAGATAGCCCTGGACAAACAATGCCACGAAGCAGAAG 3' (SEQ ID NO: 3).

There were four probes against p53, the first (hybridizing to a portion of exon 5) was 5'TACTCCCCTGCCCTCAACAAGATGTTTTGCCAACTGG3' (SEQ ID NO:4), the second (hybridizing to a portion of exon 7) was 5'ATTTCTTCCATACTACTACCCATCGACCTCTCATC3' (SEQ ID NO: 5), the third, also hybridizing to a portion of exon 7 was 5'ATGAGGCCAGTGCGCCTTGGGGAGACCTGTGGCAAGC3' (SEQ ID NO: 6); and finally, a probe against exon 8 had the sequence 5'GAAAGGACAAGGGTGGTTGGGAGTAGATGGAGCCTGG3' (SEQ ID NO: 7).

A 10 µl aliquot of each probe (20 pmol/capture) was added to a suspension containing 300 µl DNA in the presence of 310 µl 6M GITC buffer for 2 hours at room temperature. Hybrid complexes were isolated using streptavidin-coated beads (Dynal). After washing, probe-bead complexes were suspended at 25° C. for 1 hour in 0.1×TE buffer, pH7.4. The suspension was then heated for 4 minutes at 85° C., and the beads were removed.

Captured DNA was then amplified using PCR, essentially as described in U.S. Pat. No. 4,683,202, incorporated by reference herein. Each sample was amplified using forward and reverse primers through 7 loci (Kras, exon 1, APC exon 15 (3 separate loci), p53, exon 5, p53, exon 7, and p53, exon 8) in duplicate (for a total of 14 amplifications for each locus). Seven separate PCRs (40 cycles each) were run in duplicate using primers directed to detect fragments in the sample having 200 base pairs or more. Amplified DNA was placed on a 4% Nusieve (FMC Biochemical) gel (3% Nusieve, 1% agarose), and stained with ethidium bromide (0.5 µg/ml). The resulting amplified DNA was graded based upon the relative intensity of the stained gels. The results are shown in FIGS. 1-7. Each Figure represents the results for all 9 patients (including standards) for the seven different loci that were amplified. As shown in the Figures, each sample from a patient with cancer or adenoma was detected as a band having significantly greater intensity than the bands associated with samples from patients who did not have cancer or precancer. All four cancer/adenoma patients identified using colonoscopy were correctly identified by determining the amount of amplifiable DNA 200 base pairs or greater in length. As shown in FIGS. 1-7, the results were the same regardless of which locus was amplified. Accordingly, the amount of 200 bp or greater DNA in a sample was predictive of patient disease status.

Example 2

An experiment was conducted that was essentially identical to the one described above in Example 1, but forward and reverse primers were placed such that fragments of about 1.8 Kb and above were amplified.

Figure 1:
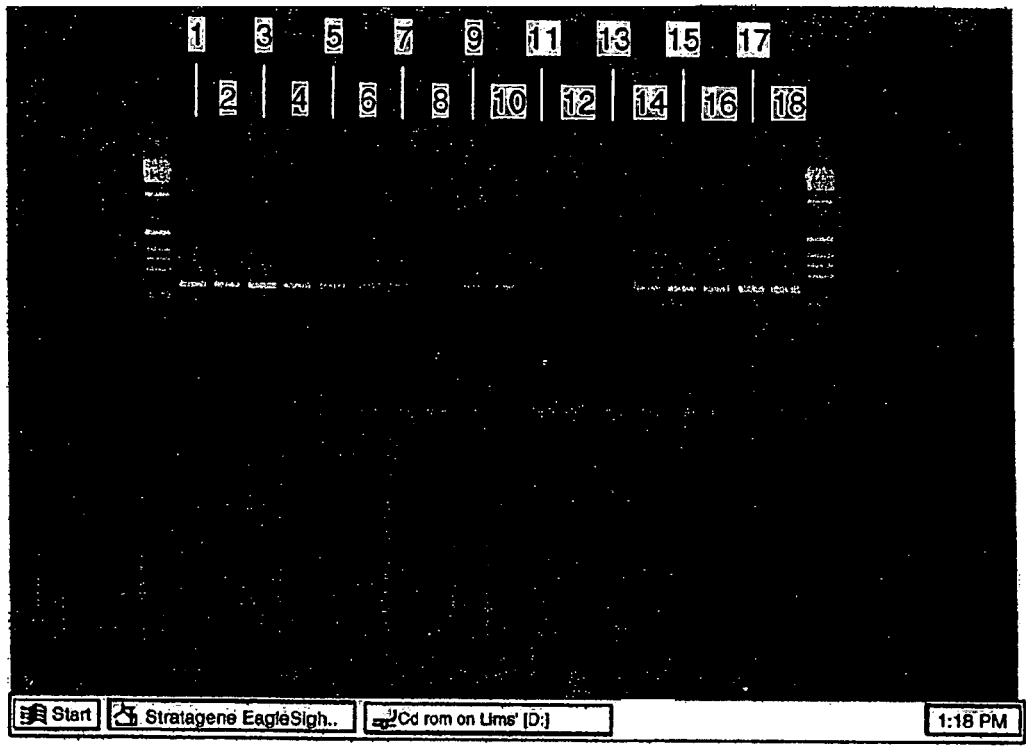
FIG. 1 is a gel photograph showing results of amplification of K-ras (exon 1) DNA isolated from stool using forward and reverse primers spaced about 200 bp apart. The band intensity relates to the amount of 200 bp product or greater in the sample. Lanes 14 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure. Amplifications were graded A through C, A being the most intense band, C being the least.
Figure 2:
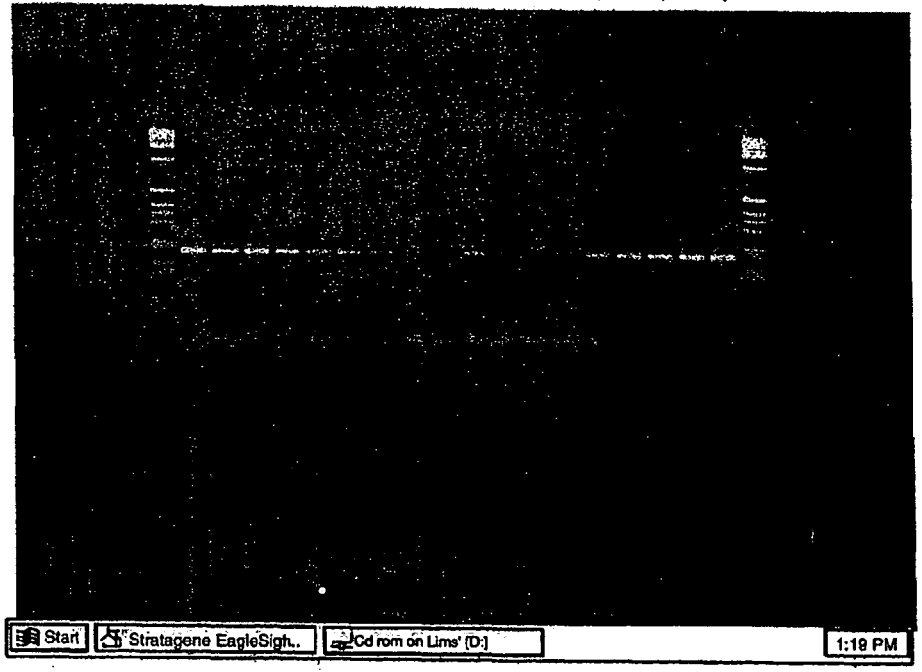
FIGS. 2-4 are gel photographs showing results of amplification of apc (exon 15) DNA isolated from stool using forward and reverse primers spaced about 200 bp apart. The band intensity relates to the amount of 200 bp product or greater in the sample. Lanes 14 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure. Amplifications were graded A through C, A being the most intense band, C being the least.
Figure 3:
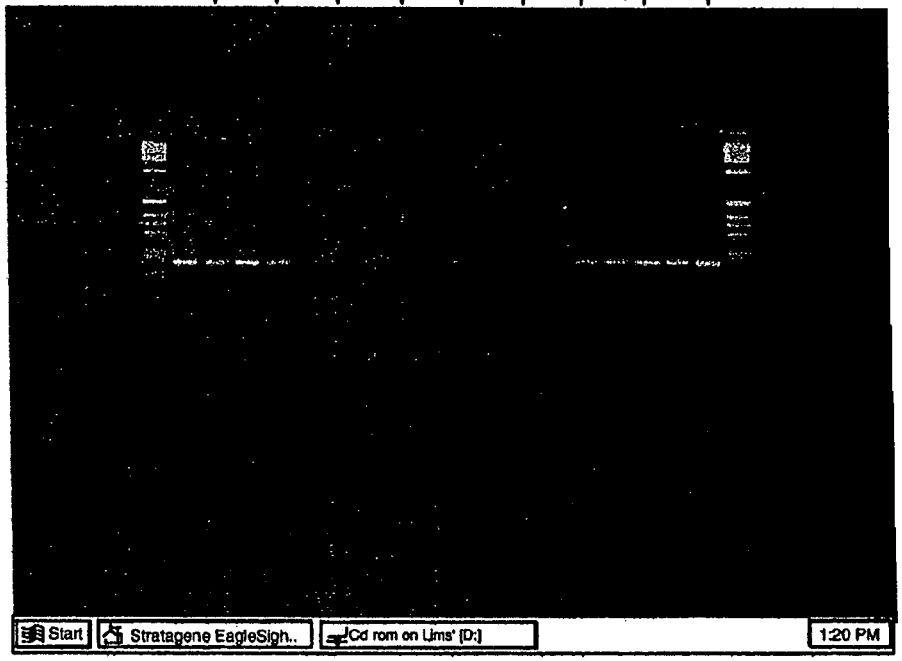
Figure 4:
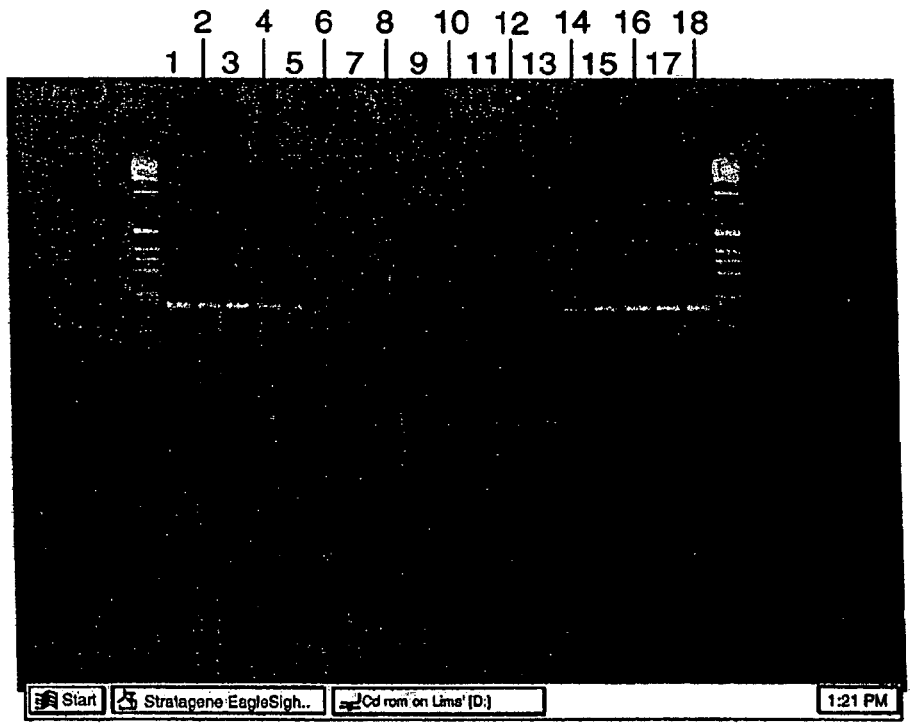
Figure 5:
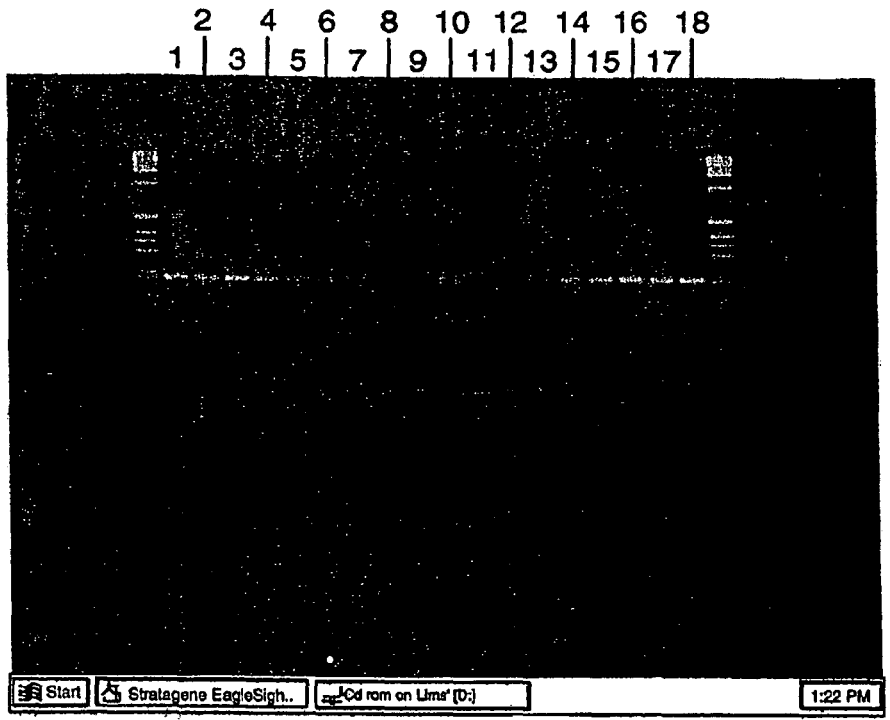
FIG. 5 is a gel photograph showing results of amplification of p53 (exon 5) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure. Amplifications were graded A through C, A being the most intense band, C being the least.
Figure 6:
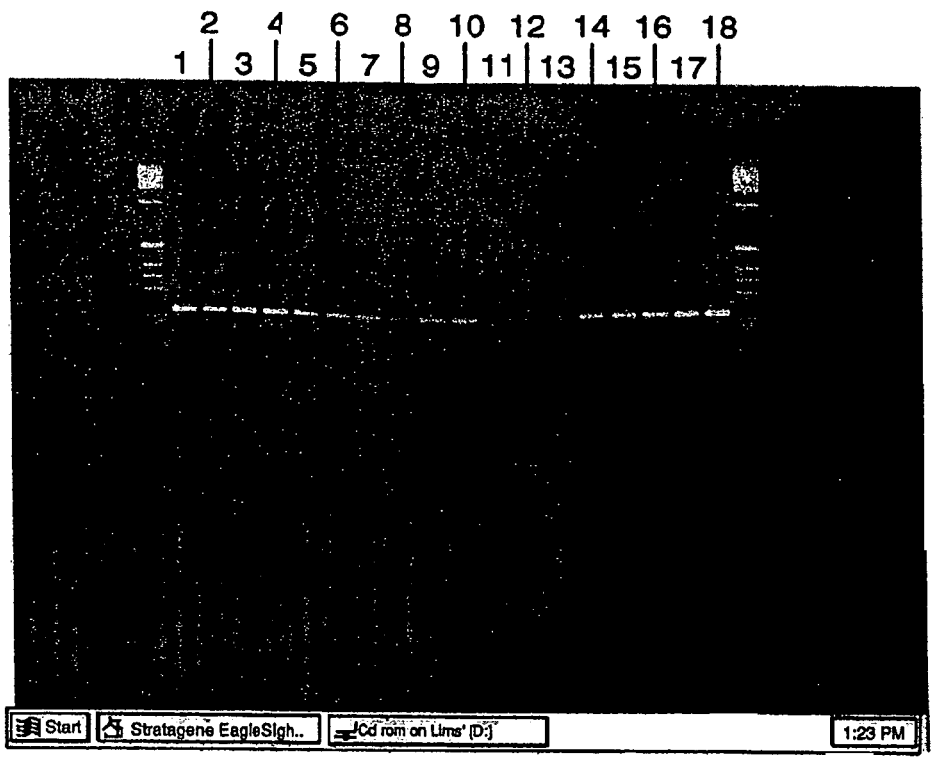
FIG. 6 is a gel photograph showing results of amplification of p53 (exon 7) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure. Amplifications were graded A through C, A being the most intense band, C being the least.
Figure 7:
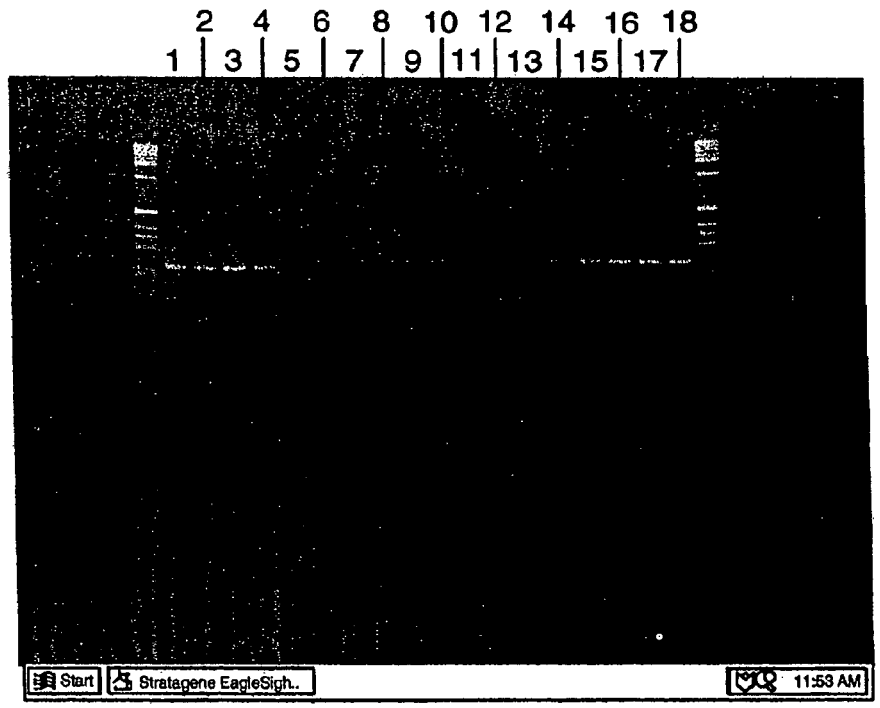
FIG. 7 is a gel photograph showing results of amplification of p53 (exon 8) DNA isolated from stool using forward and reverse primers spaced about 200 bp apart. The band intensity relates to the amount of 200 bp product or greater in the sample. Lanes 1-4 are results from patients with cancer or adenoma, lane 5 is a positive control, lanes 6-10 are from patients who did not have cancer or adenoma, lanes 11-12 are negative controls, and lanes 13-18 are standards at the approximate molecular weight indicated in the figure. Amplifications were graded A through C, A being the most intense band, C being the least.
Figure 8:
Figure 9:
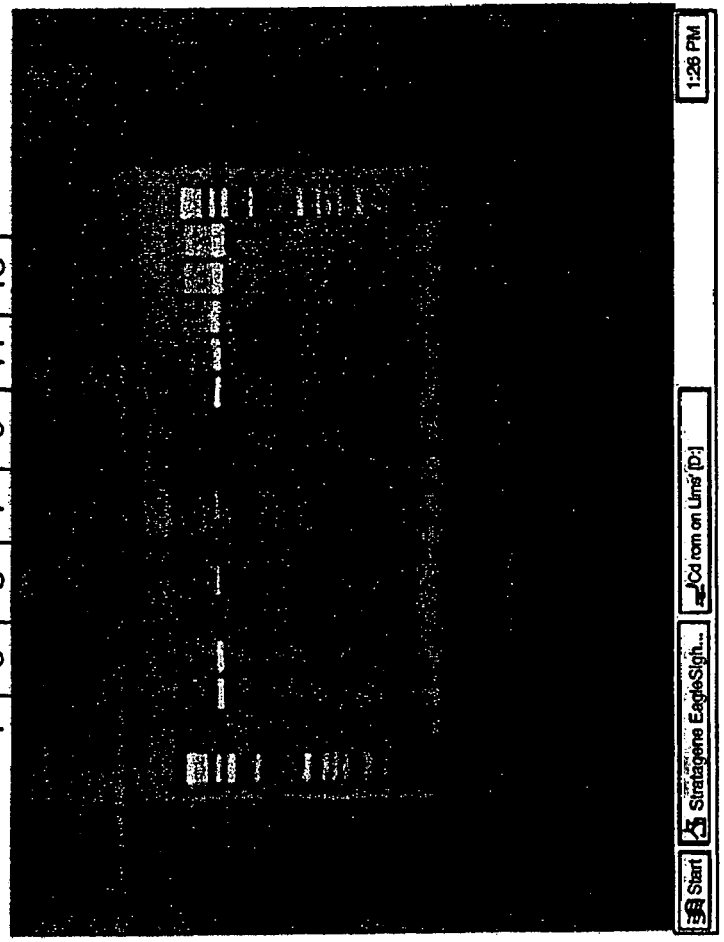
FIG. 9-10 are gel photographs of results of amplification of DNA from stool samples using forward and reverse primers spaced approximately 1.8 Kb apart. The band intensity shows the amount of 1.8 Kb or greater product. Lanes 1, 8, and 9 are negative controls, lanes 2, 3, and 5 are results from patients with cancer or adenoma, lanes 4, 6, and 7 are results from patients who did not have cancer or adenoma, and lanes 10-14 are molecular weight standards.
Figure 10:
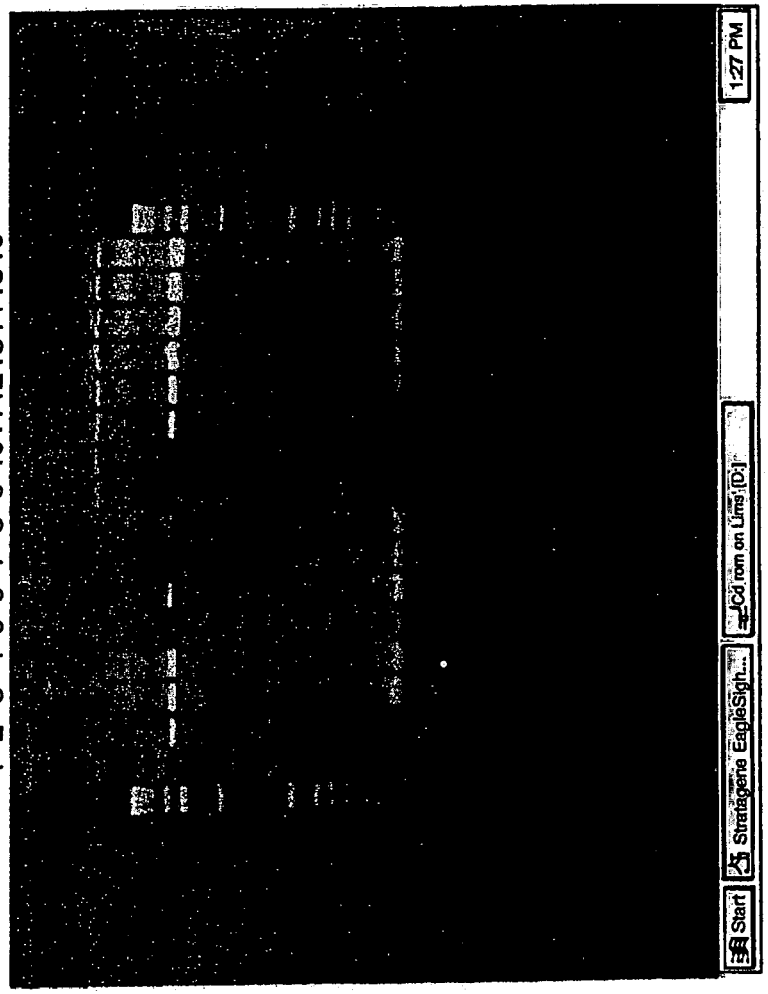

DNA was prepared as described above. Forward and reverse primers were spaced so as to hybridize approximately 1.8 Kb apart on three different loci (Kras, exon 1, APC, exon 15, and p53 exon 5). Thirty-three rounds of amplification were performed, and the resulting DNA was placed on a 3% agarose gel. The results are shown in FIGS. 8-10. As shown in the Figures (which show results from three separate experiments to amplify and detect "long" product), samples from individuals having cancer or precancer produced large amounts of high-molecular weight (in this case 1.8 Kb and above) DNA; whereas samples from patients who did not have cancer or precancer produced no DNA in the range of about 1.8 Kb and higher. Thus, the presence of high-molecular weight DNA was indicative of the disease status of the patient.

Example 3

An experiment was conducted to determine the molecular weight profile of DNA from samples collected and prepared as part of a blind study on 30 patients who presented at the Mayo Clinic with suspected gastrointestinal disorders. Stool samples were obtained, and DNA was isolated as described above.

Prior to amplification, DNA was isolated from the samples by hybrid capture. Biotynilated probes against portions of the BRCA1, BRCA2, p53, APC genes were used.

The BRCA1 was 5'GATTCTGAAGAACCAACTTTGTCCTTAACTAGCTCTT3' (SEQ ID NO: 8).

The BRCA2 was 5'CTAAGTTTGAATCCATGCTTTGCTCTTCTTGATTATT3' (SEQ ID NO: 9).

The APC1 was 5'CAGATAGCCCTGGACAAACCATGCCACCAAGCAGAAG3' (SEQ ID NO: 10).

The p53 probe, hybridizing to a portion of exon 5, was 5'TACTCCCCTGCCCTCAACAAGATGTTTTGCCAACTGG3' (SEQ ID NO: 4).

The APC2 was 5'GAAGTTCCTGGATTTTCTGTTGCTGGATGGTAGTTGC3' (SEQ ID NO: 11).

A 300 µl aliquot of sample was placed in 300 µl of 6 M guanidine isothiocyanate buffer with 10 µl of each capture probe, and incubated overnight at 25 C. Captured DNA was isolated using 100 µl capture beads incubated for one hour at room temperature. The DNA was eluted off the beads and PCR amplified under standard PCR conditions.

Figure 11A:
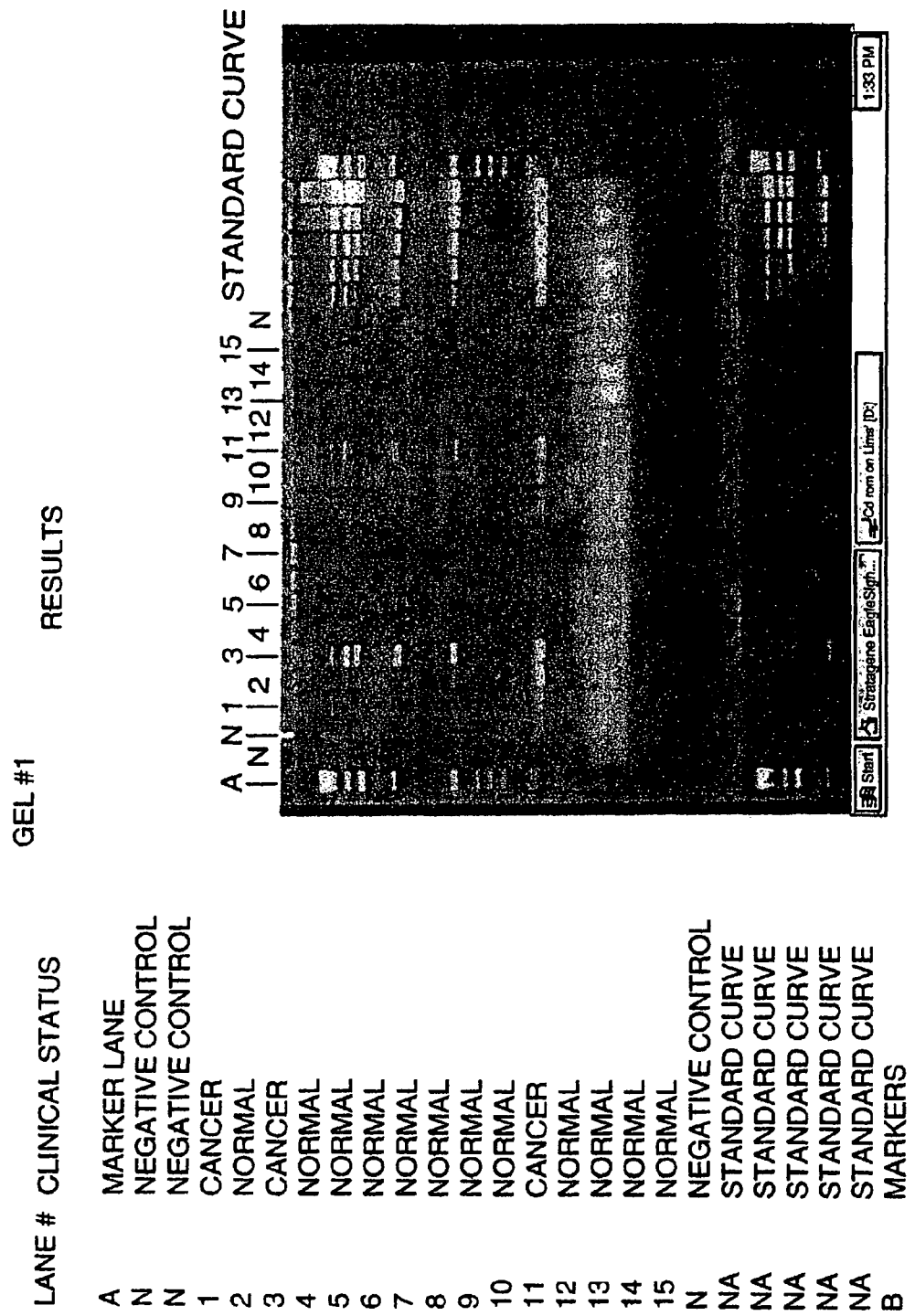
FIGS. 11A and B are gel photographs of results of amplification of DNA in stool from a total of 30 patients and controls. The band intensity relates to the amount of amplifiable DNA in the sample. Lanes N are negative controls, lanes 1, 3, 11, and 18 are results from patients which are indicative of the presence off cancer or adenoma, lanes 2, 4, 5-10, 12-17, and 19-30 are results from patients which are indicative of the absence of cancer or adenoma. The remaining lanes are markers or standards.
Figure 11B:
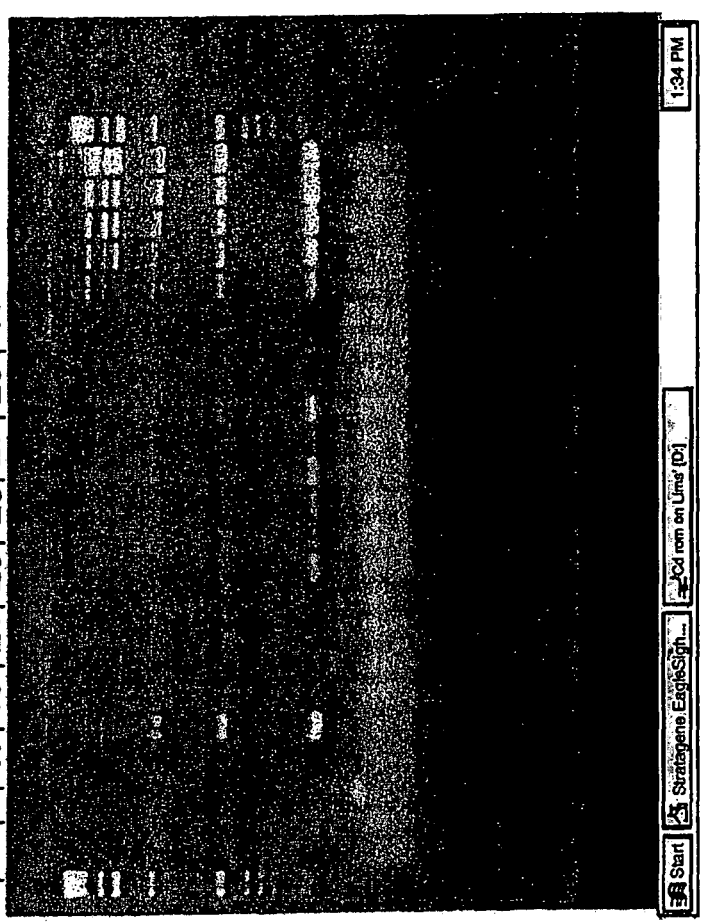

According to methods of the invention, amplification reactions were conducted using forward and reverse primers through the 5 loci for each sample. Forward and reverse primers were spaced to amplify fragments of 200 bp, 400 bp, 800 bp, 1.3 Kb, 1.8 Kb, and 2.4 Kb. Each of 30 PCR reactions was run for 36 cycles. Amplicon was run on a 3% Seakeam gel, and stained with ethidium bromide. The results are shown in FIGS. 11A and 11B. Each figure represents the results for 15 of the 30 patients.

As shown in those figures, patients with cancer or adenoma have an increased yield of amplifiable DNA. That is especially true at the 1.8 Kb level and above. Thus, patients with cancer or adenoma not only produce more amplifiable DNA in their stool, but also produce larger DNA fragments than are produced in the stool of patients who do not have cancer. Thus, both an increased yield of amplifiable DNA and the presence of high molecular weight DNA, especially that at 1.8 Kb and above, were indicative of patient disease status.

Example 4

In this example, methods of the invention were correlated with clinical outcome in numerous patients who had a colorectal adenoma or colorectal cancer as diagnosed using colonoscopy, and 79 patients who were diagnosed as not having colorectal cancer or adenoma. A stool sample was obtained from each of these patients and prepared as described above. Fragments of the 5 different loci referred to above were amplified using primers spaced 200, 400, 800, 1300, 1800, and 2400 base pairs apart using the protocol described above in Example 3. Each amplification was scored such that successful amplification of a fragment received a score of 1, and no amplification received a score of 0. Since five loci were interrogated using 6 primer pairs each, the maximum score was 30 (successful amplification of all 6 fragments at all five loci). The cutoff for a positive screen was set at 21. The results are shown below.

TABLE 1

Normals

| Patient No. | Age | Score |
|---|---|---|
| P-178 | 64 | 19 |
| P-185 | 50 | 18 |
| P-033 | 56 | 16 |
| P-177 | 67 | 14 |
| P-055 | 75 | 13 |
| P-029 | 70 | 12 |
| P-079 | 63 | 12 |
| P-066 | 72 | 11 |
| P-027 | 65 | 10 |
| P-054 | 72 | 9 |
| P-158 | 59 | 9 |
| P-043 | 56 | 8 |
| P-009 | 73 | 7 |
| P-030 | 86 | 2 |
| P-032 | 51 | 1 |
| P-068 | 58 | 1 |
| P-187 | 63 | 1 |
| P-018 | 68 | 0 |
| P-186 | 61 | 17 |
| P-135 | 67 | 14 |
| P-120 | 75 | 13 |
| P-179 | 76 | 9 |
| P-057 | 56 | 7 |
| P-143 | 65 | 6 |
| P-136 | 58 | 1 |
| P-012 | 75 | 0 |

TABLE 2

Adenomas

| Patient No. | Age | Score |
|---|---|---|
| P-003 | | 29 |
| P-001 | | 23 |
| P-045 | | 22 |
| P-162 | | 21 |
| P-163 | | 16 |
| P-088 | | 15 |
| P-050 | | 13 |
| P-060 | | 11 |
| P-061 | | 11 |
| P1058 | | 10 |
| P-075 | | 10 |
| P-077 | | 8 |
| P-024 | | 7 |
| P-056 | | 7 |
| P-067 | | 7 |
| P-025 | | 6 |
| P-080 | | 4 |
| P-123 | | 4 |
| P-048 | | 3 |
| P-040 | | 2 |
| P-006 | | 1 |
| P-004 | | 0 |
| P-015 | | 0 |
| P-083 | | 0 |

TABLE 2-continued

Adenomas

| Patient No. | Age | Score |
|---|---|---|
| P-047 | | |
| P-129 | | |

TABLE 3

Carcinomas

| Patient No. | Age | Score |
|---|---|---|
| P-064 | | 30 |
| P-103 | | 30 |
| P-104 | | 30 |
| P-108 | | 30 |
| P-101 | | 29 |
| P-102 | | 29 |
| P-099 | | 28 |
| P-107 | | 28 |
| P-110 | | 26 |
| P-098 | | 25 |
| P-134 | | 24 |
| P-062 | | 23 |
| P-090 | | 23 |
| P-095 | | 23 |
| P-093 | | 22 |
| P-100 | | 21 |
| P-122 | | 18 |
| P-084 | | 15 |
| P-109 | | 15 |
| P-118 | | 10 |
| P-138 | | 10 |
| P-091 | | 8 |
| P-096 | | 8 |
| P-053 | | 7 |
| P-119 | | 6 |
| P-117 | | 5 |
| P-105 | | 0 |
| P-097 | | |

As shown above, methods of the invention are effective in screening for the presence of colorectal cancer and adenoma.

Example 5

In this example, methods of the invention were used to detect non-colonic cancers in 28 patients.

A stool sample was obtained from each of the 28 patients. The sample was prepared as described above. Fragments of the 5 different loci referred to above were amplified using primers spaced 200, 400, 800, 1300, 1800, and 2400 base pairs apart using the protocol described above in Example 3. Each amplification was scored such that successful amplification of a fragment received a score of 1, and no amplification received a score of 0. Since five loci were interrogated using 6 primer pairs each, the maximum obtainable score was 30 (successful amplification of all 6 fragments at all five loci). A score of 21 was used as a cutoff between diseased and non-diseased patients. The results are shown below.

TABLE 4

Supercolonic Cancers

| Patient No. | Supercolonic Cancer | Age | Score |
|---|---|---|---|
| P-145 | Pancreas | 68 | 30 |
| P-164 | Lung CA | 68 | 30 |
| P-166 | Bile Duct | 52 | 30 |

TABLE 4-continued

Supercolonic Cancers

| Patient No. | Supercolonic Cancer | Age | Score |
|---|---|---|---|
| P-189 | Bile Duct | 43 | 30 |
| P-190 | Lung CA | 50 | 30 |
| P-019 | Atypical Findings in Stomach | 71 | 29 |
| P-152 | Lung CA | 77 | 28 |
| P-167 | Pancreas | 72 | 28 |
| P-011 | Lung CA | 73 | 27 |
| P-153 | Pancreas | 65 | 27 |
| P-165 | Lung CA | 85 | 27 |
| P-170 | Duodenum | 65 | 27 |
| P-182 | Barrett's Esophagus | 58 | 27 |
| P-146 | Bile Duct | 63 | 26 |
| P-081 | Barrett's Esophagus | 74 | 26 |
| P-151 | Pancreas | 49 | 25 |
| P-155 | Lung CA | 60 | 25 |
| P-156 | Lung CA | 57 | 25 |
| P-150 | Pancreas | 78 | 23 |
| P-149 | Esophagus | 59 | 19 |
| P-154 | Esophagus | 80 | 19 |
| P-169 | Pancreas | 71 | 19 |
| P-168 | Lung CA | 63 | 18 |
| P-180 | Pancreas | 67 | 13 |
| P-144 | Esophagus | 59 | 9 |
| P-147 | Stomach | 57 | 7 |
| P-148 | Stomach | 69 | 6 |
| P-171 | Esophagus | 76 | 0 |

As shown above, methods of the invention successfully screened 18 out of 27 patients who actually had non-colonic cancer. Only one patient was misdiagnosed as having cancer when he did not. Thus, the methods of the invention are useful for non-invasive diagnosis of a non-specified cancerous disease state in a patient.

The threshold of 21 for a positive screen can be changed to accommodate desired sensitivities and specificities. For example, if 18 were the false negative results shown in Table 4 would be avoided. The skilled artisan knows how to set thresholds depending on the patient (e.g., a lower threshold for patients with symptoms than patients presenting with no symptoms), the disease being diagnosed, and the desired level of sensitivity and specificity. Regardless of the threshold, the principle of the invention remains that nucleic acid integrity is a viable marker for disease, and especially for cancer.

In addition, the propensity for disease may be measured using methods of the invention. For example, periodic molecular weight profiling in accordance with the methods of the invention may be used to monitor the disease state of a patient presenting no or minimal symptoms. Such longitudinal monitoring will determine whether a patient is progressing with increasing amounts of high integrity nucleic acids—indicating the desirability for follow-up examination.

What is claimed is:

1. A method of detecting fetal abnormality, the method comprising the steps of:
   conducting a plurality of amplification reactions on a nucleic acid to produce a plurality of nucleic acid fragments of different lengths, wherein the nucleic acid is obtained from maternal blood comprising fetal cells or fetal cellular debris;
   qualitatively determining amplification level in the plurality of amplification reactions; and
   identifying fetal abnormality if the qualitative amplification level is greater than a pre-determined threshold level.

2. The method of claim 1, wherein the fetal abnormality is associated with genomic instability.

3. The method of claim 1, wherein the step of qualitatively determining comprises:
   assigning a binary score to each reaction such that the binary score indicates if a positive amplification takes place; and
   determining a total score indicative of the amplification level for the plurality of amplification reactions based on the binary score in each reaction.

4. The method of claim 1, wherein the plurality of amplification reactions are conducted at a single genomic locus.

5. The method claim 1, wherein the plurality of amplification reactions are conducted on a plurality of different genomic loci.

6. The method of claim 1, wherein the pre-determined threshold level is the level of amplification determined in a normal sample.

7. The method of claim 1, wherein at least one amplified nucleic acid fragment is at least 200 bp in length.

8. The method of claim 1, wherein at least one amplified nucleic acid fragment is at least 400 bp in length.

9. The method of claim 1, wherein at least one amplified nucleic acid fragment is at least 800 bp in length.

10. The method of claim 1, wherein at least one amplified nucleic acid fragment is at least 1.3 Kb in length.

11. The method of claim 1, wherein at least one amplified nucleic acid fragment is at least 1.8 Kb in length.

12. The method of claim 1, wherein at least one amplified nucleic acid fragment is at least 2.4 Kb in length.

* * * * *

SEQUENCE LISTING

```
<160> NUMBER OF SEQ ID NOS: 11

<210> SEQ ID NO 1
<211> LENGTH: 37
<212> TYPE: DNA
<213> ORGANISM: Artificial Sequence
<220> FEATURE:
<223> OTHER INFORMATION: K-ras probe

<400> SEQUENCE: 1
gtggagtatt tgatagtgta ttaaccttat gtgtgac                              37

<210> SEQ ID NO 2
<211> LENGTH: 37
<212> TYPE: DNA
<213> ORGANISM: Artificial Sequence
<220> FEATURE:
<223> OTHER INFORMATION: APC-1309 probe

<400> SEQUENCE: 2
ttccagcagt gtcacagcac cctagaacca aatccag                              37

<210> SEQ ID NO 3
<211> LENGTH: 37
<212> TYPE: DNA
<213> ORGANISM: Artificial Sequence
<220> FEATURE:
<223> OTHER INFORMATION: APC-1378 probe

<400> SEQUENCE: 3
```

-continued cagatagccc tggacaaaca atgccacgaa gcagaag      37

<210> SEQ ID NO 4
<211> LENGTH: 37
<212> TYPE: DNA
<213> ORGANISM: Artificial Sequence
<220> FEATURE:
<223> OTHER INFORMATION: p53 probe

<400> SEQUENCE: 4
tactcccctg ccctcaacaa gatgttttgc caactgg      37

<210> SEQ ID NO 5
<211> LENGTH: 35
<212> TYPE: DNA
<213> ORGANISM: Artificial Sequence
<220> FEATURE:
<223> OTHER INFORMATION: p53 probe

<400> SEQUENCE: 5
atttcttcca tactactacc catcgacctc tcatc      35

<210> SEQ ID NO 6
<211> LENGTH: 37
<212> TYPE: DNA
<213> ORGANISM: Artificial Sequence
<220> FEATURE:
<223> OTHER INFORMATION: p53 probe

<400> SEQUENCE: 6
atgaggccag tgcgccttgg ggagacctgt ggcaagc      37

<210> SEQ ID NO 7
<211> LENGTH: 37
<212> TYPE: DNA
<213> ORGANISM: Artificial Sequence
<220> FEATURE:
<223> OTHER INFORMATION: p53 probe

<400> SEQUENCE: 7
gaaaggacaa gggtggttgg gagtagatgg agcctgg      37

<210> SEQ ID NO 8
<211> LENGTH: 37
<212> TYPE: DNA
<213> ORGANISM: Artificial Sequence
<220> FEATURE:
<223> OTHER INFORMATION: BRAC1 probe

<400> SEQUENCE: 8
gattctgaag aaccaacttt gtccttaact agctctt      37

<210> SEQ ID NO 9
<211> LENGTH: 37
<212> TYPE: DNA
<213> ORGANISM: Artificial Sequence
<220> FEATURE:
<223> OTHER INFORMATION: BRCA2 probe

<400> SEQUENCE: 9
ctaagtttga atccatgctt tgctcttctt gattatt      37

<210> SEQ ID NO 10
<211> LENGTH: 37
<212> TYPE: DNA
<213> ORGANISM: Artificial Sequence

```
<220> FEATURE:
<223> OTHER INFORMATION: APC1 probe

<400> SEQUENCE: 10
cagatagccc tggacaaacc atgccaccaa gcagaag                                37

<210> SEQ ID NO 11
<211> LENGTH: 37
<212> TYPE: DNA
<213> ORGANISM: Artificial Sequence
<220> FEATURE:
<223> OTHER INFORMATION: APC2 probe

<400> SEQUENCE: 11
gaagttcctg gattttctgt tgctggatgg tagttgc                                37
```